(12) United States Patent
Bhimavarapu et al.

(10) Patent No.: US 12,714,787 B2
(45) Date of Patent: Aug. 25, 2026

(54) COMMUNICATION SYSTEM FOR PATIENT SUPPORT APPARATUSES

(71) Applicant: Stryker Corporation, Kalamazoo, MI (US)

(72) Inventors: Krishna Sandeep Bhimavarapu, Kalamazoo, MI (US); Joshua Elmer Mix, Portage, MI (US)

(73) Assignee: Stryker Corporation, Portage, MI (US)

(*) Notice: Subject to any disclaimer, the term of this patent is extended or adjusted under 35 U.S.C. 154(b) by 593 days.

(21) Appl. No.: 18/205,714

(22) Filed: Jun. 5, 2023

(65) Prior Publication Data

US 2023/0390492 A1 Dec. 7, 2023

Related U.S. Application Data

(60) Provisional application No. 63/349,369, filed on Jun. 6, 2022.

(51) Int. Cl.

| | |
|---|---|
| ***A61M 5/172*** | (2006.01) |
| ***A61G 7/018*** | (2006.01) |
| ***A61G 7/05*** | (2006.01) |
| ***A61M 5/14*** | (2006.01) |
| ***G16H 10/60*** | (2018.01) |

(Continued)

(52) U.S. Cl.

CPC ........... *A61M 5/1723* (2013.01); *A61G 7/018* (2013.01); *A61G 7/0524* (2016.11); *A61G 7/0527* (2016.11); *A61M 5/1415* (2013.01); *G16H 10/60* (2018.01); *G16H 20/17* (2018.01);

(Continued)

(58) Field of Classification Search

CPC . A61M 5/1723; A61M 5/1415; A61G 7/0527; A61G 2203/30; A61G 2203/32; A61G 7/018; A61G 7/05; G16H 20/17; G16H 10/60; G16H 40/63

See application file for complete search history.

(56) References Cited

U.S. PATENT DOCUMENTS

| | | | |
|---|---|---|---|
| 7,242,306 | B2 | 7/2007 | Wildman et al. |
| 7,570,152 | B2 | 8/2009 | Smith et al. |

(Continued)

OTHER PUBLICATIONS

Vocera, Software Maintenance and Technical Support, published prior to Jun. 28, 2022.

*Primary Examiner* — John A Tweel, Jr.
(74) *Attorney, Agent, or Firm* — Gardner, Linn, Burkhart & Ondersma LLP

(57) ABSTRACT

A patient support apparatus for supporting a patient includes first, second, and third transceivers mounted at first, second, and third locations, respectively. A controller is adapted to use radio frequency communication between the first, second, and third transceivers and an infusion pump to determine a position of the infusion pump relative to the patient support apparatus. The controller, and/or a server in communication with the controller, is configured to double-check a dosage of medication being delivered via the infusion pump to the patient in order to help avoid incorrect dosing. The controller and/or server are adapted to automatically retrieve dosage information from the infusion pump, either directly or indirectly, and use the dosage information in combination with the patient's weight, as determined by a scale system on the patient support apparatus, to issue an alert if too high of a dosage is being administered to the patient.

20 Claims, 5 Drawing Sheets

(51) Int. Cl.
*G16H 20/17* (2018.01)
*G16H 40/63* (2018.01)

(52) U.S. Cl.
CPC ......... *G16H 40/63* (2018.01); *A61G 2203/30* (2013.01); *A61G 2203/32* (2013.01)

(56) References Cited

U.S. PATENT DOCUMENTS

| | | | | |
|---|---|---|---|---|
| 8,334,777 | B2 | 12/2012 | Wilson et al. | |
| 8,756,078 | B2 | 6/2014 | Collins, Jr. et al. | |
| 9,446,186 | B2 * | 9/2016 | Estes | A61M 5/14244 |
| 9,569,591 | B2 | 2/2017 | Vanderpohl, III | |
| 9,571,985 | B2 | 2/2017 | Bottazzi et al. | |
| 9,593,522 | B1 | 3/2017 | Murar et al. | |
| 9,788,151 | B2 | 10/2017 | Duan et al. | |
| 10,064,012 | B1 | 8/2018 | Boston et al. | |
| 10,231,649 | B2 | 3/2019 | Bhimavarapu et al. | |
| 10,474,808 | B2 | 11/2019 | Huster | |
| 10,608,699 | B2 | 3/2020 | Nabki et al. | |
| 10,811,136 | B2 | 10/2020 | Bhimavarapu et al. | |
| 10,846,961 | B2 | 11/2020 | de Perthuis et al. | |
| 10,905,520 | B2 | 2/2021 | Desaulniers | |
| 10,994,077 | B2 * | 5/2021 | Rosinko | A61M 5/142 |
| 11,026,067 | B2 | 6/2021 | Martin et al. | |
| 11,120,906 | B2 * | 9/2021 | Gandy | G09B 7/00 |
| 11,153,810 | B2 | 10/2021 | Yoon et al. | |
| 11,289,194 | B1 | 3/2022 | Pipher et al. | |
| 11,378,644 | B2 | 7/2022 | Hsieh | |
| 11,400,889 | B2 | 8/2022 | Parthasarathi et al. | |
| 11,610,671 | B2 | 3/2023 | Hochworter | |
| 11,984,221 | B2 * | 5/2024 | Bodurka | H04W 4/029 |
| 12,186,241 | B2 * | 1/2025 | Williams | G16H 40/20 |
| 2008/0120784 | A1 | 5/2008 | Warner et al. | |
| 2008/0312971 | A2 | 12/2008 | Rosow et al. | |
| 2011/0208541 | A1 | 8/2011 | Wilson et al. | |
| 2014/0080413 | A1 * | 3/2014 | Hayes | H04B 5/266<br>455/41.1 |
| 2014/0297327 | A1 | 10/2014 | Heil et al. | |
| 2015/0291127 | A1 | 10/2015 | Ghabra | |
| 2016/0140307 | A1 | 5/2016 | Brosnan et al. | |
| 2017/0287316 | A1 | 10/2017 | Wildman et al. | |
| 2021/0065885 | A1 | 3/2021 | Receveur et al. | |
| 2022/0088305 | A1 * | 3/2022 | Cavendish, Jr. | G16H 40/63 |
| 2022/0241124 | A1 | 8/2022 | Bhimavarapu et al. | |

* cited by examiner

COMMUNICATION SYSTEM FOR PATIENT SUPPORT APPARATUSES

CROSS-REFERENCE TO RELATED APPLICATIONS

This application claims priority to U.S. provisional patent application Ser. No. 63/349,369 filed Jun. 6, 2022, by inventors Krishna Sandeep Bhimavarapu et al. and entitled COMMUNICATION SYSTEM FOR PATIENT SUPPORT APPARATUSES, the complete disclosure of which is incorporated herein by reference.

BACKGROUND

The present disclosure relates to patient support apparatuses, such as beds, cots, stretchers, recliners, or the like. More specifically, the present disclosure relates to patient support apparatuses that communicate with one or more devices that are separate from the patient support apparatus itself.

Patients in hospitals often have one or more infusion pumps that deliver medications to the patient. The rate at which the infusion pump delivers the medication to the patient is important to the health and well-being of the patient. Typically, this rate is dependent upon the weight of the patient, with larger patients able to accept a higher dose and/or rate than smaller patients.

SUMMARY

According to the various aspects described herein, the present disclosure is directed to a patient support apparatus and system that helps reduce medication deliver errors. More specifically, the present disclosure is directed to a system that double checks the patient's weight, as measured by a patient support apparatus, with dosage information relating to a medication that is being delivered to a patient via an infusion pump. The system automatically checks to see if the dosage information is within an acceptable threshold based upon the patient's measured weight. An alert is provided via the patient support apparatus and/or a mobile electronic device associated with a caregiver if the dosage information is outside of an acceptable threshold. The system of the present disclosure therefore provides an automated double-checking function to help ensure that patients are not administered medications at an incorrect dosage. These and other aspects of the present disclosure will be apparent to a person of ordinary skill in light of the following written description and accompanying drawings.

According to a first aspect of the present disclosure, a patient support apparatus is provided that includes a support surface; a scale system; a first transceiver coupled to a first location on the patient support apparatus; a second transceiver coupled to a second location on the patient support apparatus; a third transceiver coupled to a third location on the patient support apparatus; and a controller. The scale system is adapted to determine a weight of the patient. The controller is adapted to use radio frequency (RF) communication between the first, second, and third transceivers and an infusion pump to determine a position of the infusion pump relative to the patient support apparatus. The controller is further adapted to: receive an identifier from the infusion pump; determine if the infusion pump is positioned inside or outside of a volume of space, and to send both the weight of the patient and the infusion pump identifier to a server if the infusion pump is positioned inside the volume of space.

According to another aspect of the present disclosure, a patient support apparatus is provided that includes a support surface; a scale system; a first transceiver coupled to a first location on the patient support apparatus; a second transceiver coupled to a second location on the patient support apparatus; a third transceiver coupled to a third location on the patient support apparatus; and a controller. The scale system is adapted to determine a weight of the patient. The controller is adapted to use radio frequency (RF) communication between the first, second, and third transceivers and an infusion pump to determine a position of the infusion pump relative to the patient support apparatus. The controller is further adapted to determine if the infusion pump is positioned inside or outside of a volume of space, and to send the weight of the patient to the infusion pump if the infusion pump is positioned inside the volume of space.

According to still another aspect of the present disclosure, a patient support apparatus system is provided that includes a patient support apparatus and a server. The patient support apparatus includes a support surface adapted to support a patient; a scale system adapted to determine a weight of the patient; a first transceiver coupled to a first location on the patient support apparatus; a second transceiver coupled to a second location on the patient support apparatus; a third transceiver coupled to a third location on the patient support apparatus; and a controller. The scale system is adapted to determine a weight of the patient. The controller is adapted to perform the following: (i) to use radio frequency (RF) communication between the first, second, and third transceivers and an infusion pump to determine a position of the infusion pump relative to the patient support apparatus, (ii) to receive an infusion pump identifier from the infusion pump, (iii) to determine if the infusion pump is positioned inside or outside of a volume of space, (iv) to send the infusion pump identifier to the server if the infusion pump is positioned inside the volume of space; (v) to use RF communication between the first, second, and third transceivers and a fixed locator to determine a position of the patient support apparatus relative to the fixed locator, (vi) to receive an identifier from the fixed locator, (vii) to determine if the patient support apparatus is positioned within a threshold distance to the fixed locator, and (viii) to forward the fixed locator identifier to the server if the patient support apparatus is positioned within the threshold distance. The server is adapted to perform the following: to use the identifier from the fixed locator to determine a patient identifier associated with the infusion pump, and to use at least one of the infusion pump identifier or the patient identifier to send a request to an Electronic Medical Records (EMR) server to receive an HL-7 feed from the infusion pump.

According to still another aspect of the present disclosure, a patient support apparatus system is provided that includes a patient support apparatus and a server. The patient support apparatus includes a support surface adapted to support a patient; a scale system adapted to determine a weight of the patient; a first transceiver coupled to a first location on the patient support apparatus; a second transceiver coupled to a second location on the patient support apparatus; a third transceiver coupled to a third location on the patient support apparatus; and a controller. The scale system is adapted to determine a weight of the patient. The controller is adapted to perform the following: (i) to use radio frequency (RF) communication between the first, second, and third transceivers and an infusion pump to determine a position of the infusion pump relative to the patient support apparatus, (ii) to receive an infusion pump identifier from the infusion pump, (iii) to determine if the infusion pump is positioned inside or outside of a volume of space, and (iv) to send the infusion pump identifier to the server if the infusion pump is positioned inside the volume of space. The server is adapted to forward data from the infusion pump to the patient support apparatus if the infusion pump is positioned inside of the volume of space.

According to other aspects of the present disclosure, the first transceiver, the second transceiver, and the third transceiver are all ultra-wideband transceivers.

In some aspects, the patient support apparatus further includes a memory in which the first location, the second location, and the third location of the first, second, and third transceivers, respectively, is stored.

The controller, in some aspects, is further adapted to use the stored locations of the first, the second, and the third transceivers to determine whether the infusion pump is positioned inside or outside of the volume of space.

In some aspects, the controller is further adapted to not send the infusion pump identifier to the server if the infusion pump is positioned outside of the volume of space.

In some aspects, the controller is further adapted to use RF communication between the first, second, and third transceivers and a fixed locator to determine a position of the patient support apparatus relative to the fixed locator.

The controller, in some aspects, is further adapted to receive an identifier from the fixed locator, to determine if the patient support apparatus is positioned within a threshold distance of the fixed locator, and to forward a fixed locator identifier to the server if the patient support apparatus is positioned within the threshold distance.

The patient support apparatus, in some aspects, further includes a microphone adapted to convert sounds of the patient's voice to audio signals. The controller may be further adapted to transmit the audio signals to the fixed locator if the fixed locator is positioned within the threshold distance, and to not transmit the audio signals to the fixed locator if the fixed locator is positioned outside of the threshold distance.

The controller, in some aspects, is further adapted to receive a message from the server if the infusion pump is determined to be inside the volume of space. The message indicates a rate at which medication is being delivered to the patient via the infusion pump. The controller is further adapted to issue an alert if the rate exceeds a threshold rate, wherein the threshold rate is based on the weight of the patient.

In some aspects, the patient support apparatus further includes a display in communication with the controller, and the controller is adapted to display data from the infusion pump on the display if the infusion pump is positioned inside the volume of space. The controller may further be adapted to not display data from the infusion pump on the display if the infusion pump is positioned outside of the volume of space.

In some aspects, the controller and/or the server is further adapted to perform the following: receive dosage information from the infusion pump if the infusion pump is positioned inside the volume of space, calculate a rate at which a medication is being infused into the patient by the infusion pump, and issue an alert if the rate exceeds a threshold rate, wherein the threshold rate is based on the weight of the patient.

In some aspects, the controller is further adapted to not send the weight of the patient to the infusion pump if the infusion pump is positioned outside of the volume of space.

In some aspects, the server is adapted to receive dosage information from the infusion pump via an HL-7 feed, to use the dosage information to calculate a rate at which a medication is being infused into the patient by the infusion pump, and to send a message to the patient support apparatus if the rate exceeds a threshold rate, wherein the threshold rate is based on the weight of the patient.

In some aspects, the HL-7 feed comes from an Electronic Medical Records (EMR) server.

Before the various aspects of the disclosure are explained in detail, it is to be understood that the claims are not to be limited to the details of operation or to the details of construction and the arrangement of the components set forth in the following description or illustrated in the drawings. The aspects described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
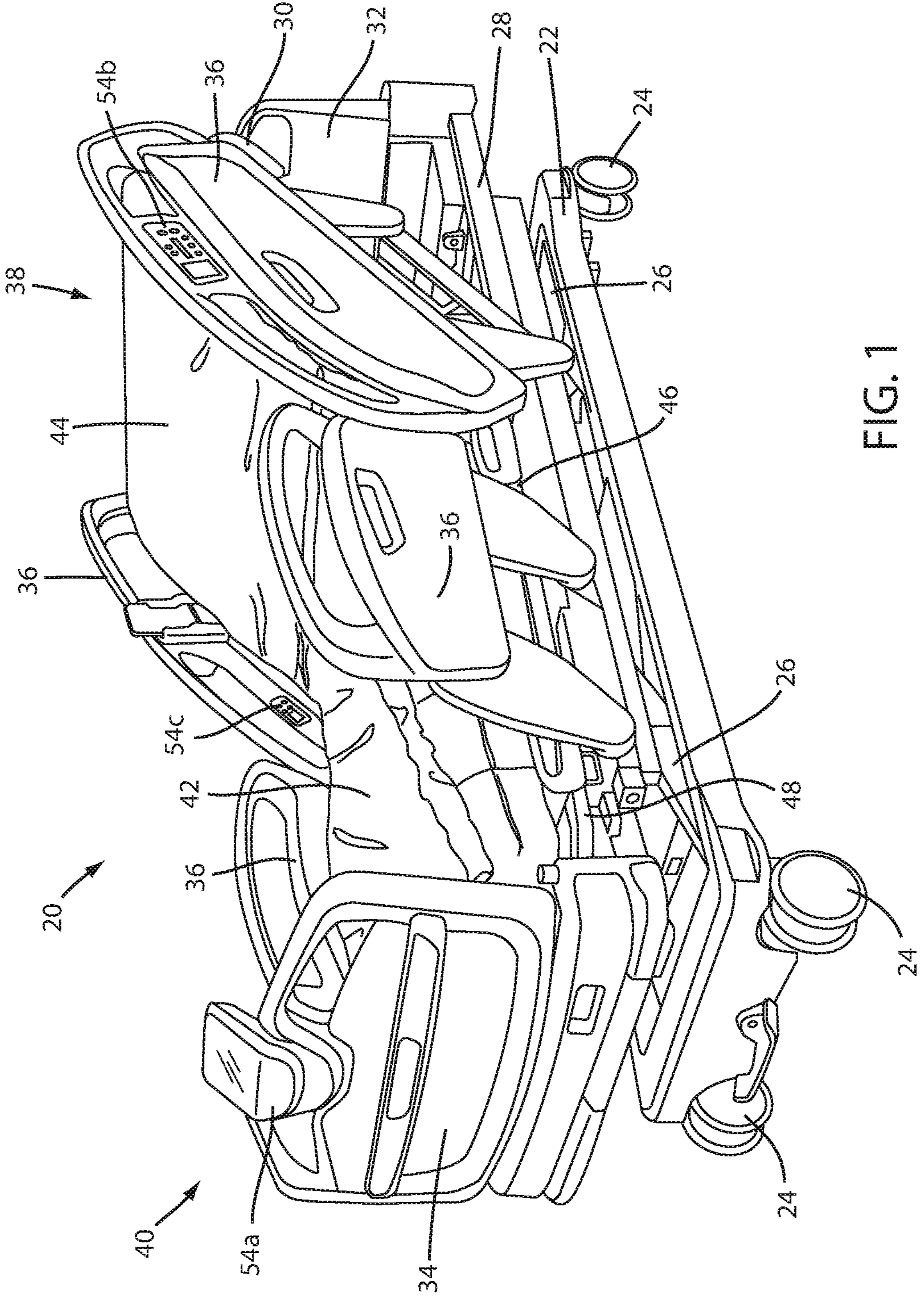
FIG. 1 is a perspective view of a patient support apparatus according to a first aspect of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. In some embodiments, the mattress 42 includes one or more inflatable bladders that are controllable via a blower, or other source of pressurized air. In at least one embodiment, the inflation of the bladders of the mattress 42 is controllable via electronics built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term “longitudinal” refers to a direction parallel to an axis between the head end 38 and the foot end 40. The terms “transverse” or “lateral” refer to a direction perpendicular to the longitudinal direction and parallel to a surface on which the patient support apparatus 20 rests.

It will be understood by those skilled in the art that patient support apparatus 20 can be designed with other types of mechanical constructions that are different from what is shown in the attached drawings, such as, but not limited to, the construction described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the mechanical construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of mechanical constructions, such as, but not limited to, those described in commonly assigned, U.S. Pat. No. 7,690,059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall mechanical construction of patient support apparatus 20 may also take on still other forms different from what is disclosed in the aforementioned references provided the patient support apparatus includes one or more of the functions, features, and/or structures discussed in greater detail below.

Figure 2:
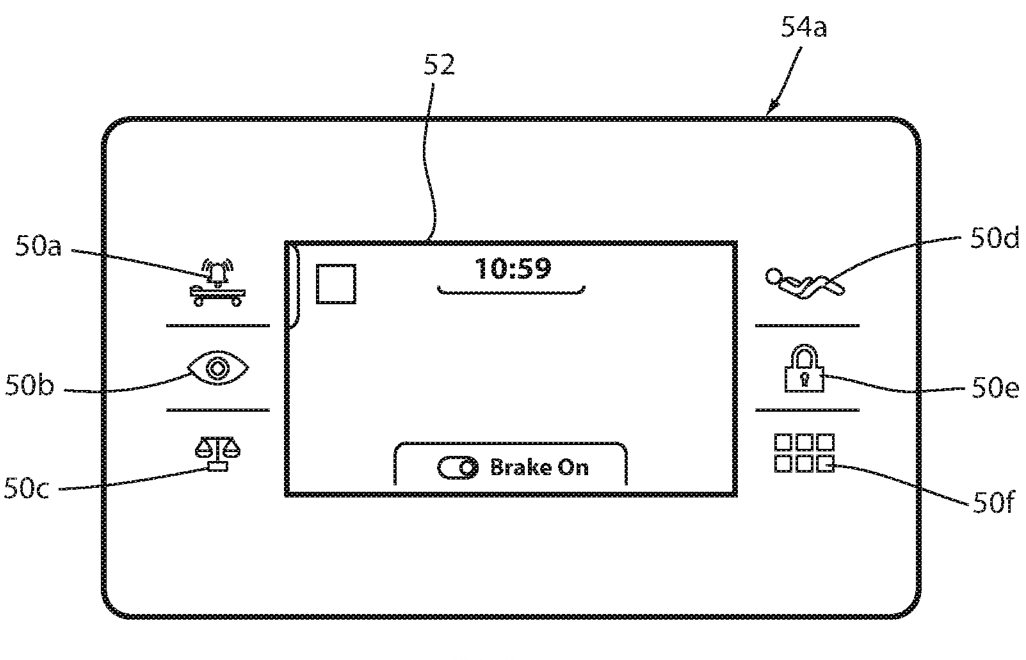
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel **54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54** does not necessarily include the same controls and/or functionality.

Among other functions, controls 50 of control panel **54*a* allow a user to control one or more of the following: change a height of support deck 30, raise or lower head section 44, activate and deactivate a brake for wheels 24, arm and disarm an exit detection system 136 (FIG. 5), change various settings on patient support apparatus 20, view the current location of the patient support apparatus 20 as determined by the location detection system discussed herein, view what medical devices, such as, but not limited to, infusion pumps, the patient support apparatus 20 has associated itself with, and perform other actions. One or both of the inner siderail control panels 54*c* also include at least one control that enables a patient to call a remotely located nurse (or other caregiver). In addition to the nurse call control, one or both of the inner siderail control panels 54***c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Figure 5:
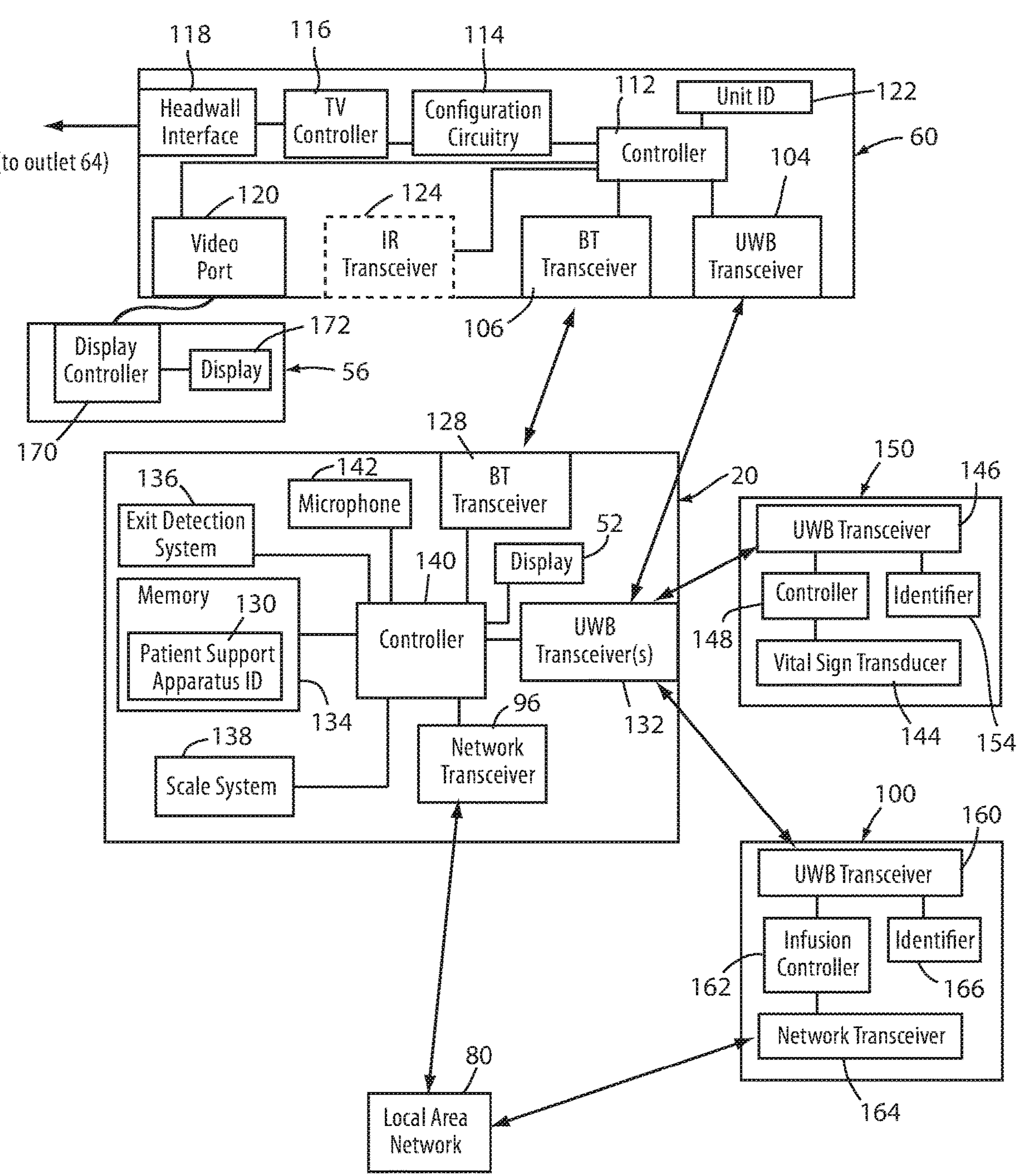
FIG. 5 is a block diagram of the patient support apparatus, the infusion pump, and the display device of FIG. 4, as well as a healthcare facility network.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system 136 (FIG. 5). The exit detection system 136 is as adapted to issue an alert when a patient exits from patient support apparatus 20. Exit detection system 136 may include any of the same features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

When a user presses navigation control 50*b* (FIG. 2), control panel 54 displays a monitoring control screen that includes a plurality of control icons that, when touched, control an onboard monitoring system built into patient support apparatus 20. The onboard monitoring system alerts the caregiver through a unified indicator, such as a light or a plurality of lights controlled in a unified manner, when any one or more of a plurality of settings on patient support apparatus 20 are in an undesired state, and uses that same unified indicator to indicate when all of the plurality of settings are in their respective desired states. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

When a user presses navigation control 50*c*, control panel 54*a* displays a scale control screen that includes a plurality of control icons that, when touched, control a scale system 138 (FIG. 5) of patient support apparatus 20. Such a scale system 138 may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors and/or other components that are utilized by the exit detection system 136, or it may utilize one or more different sensors and/or other components. Other scale systems besides those mentioned above in the '254 and '954 applications may alternatively be included within patient support apparatus 20.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50*e*, control panel 54*a* displays a motion lock control screen that includes a plurality of control icons that, when touched, control one or more motion lockout functions of patient support apparatus 20. Such motion lockout functions typically include the ability for a caregiver to use control panel 54*a* to lock out one or more of the motion controls 50 of the patient control panels 54*c* such that the patient is not able to use those controls 50 on control panels 54*c* to control the movement of one or more components of patient support apparatus 20. The motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, displaying information about one or more medical devices that are currently associated with patient support apparatus 20, diagnostic and/or service information for patient support apparatus 20, mattress control and/or status information, configuration settings, location information, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 50*f* allows a user to navigate to a screen that enables a user to see which medical devices, if any, are currently located within a predefined volume of space that encompasses patient support apparatus 20. As will be discussed in greater detail below, patient support apparatus 20 includes an onboard locating system that is adapted to automatically determine the relative position of one or more medical devices with respect to patient support apparatus 20 and, in some instances, automatically associate those devices with patient support apparatus 20 (and/or the patient assigned to patient support apparatus 20) depending upon the proximity of the medical device to patient support apparatus 20. Further details of this locating system are provided below.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* could alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls. Additionally, patient support apparatus 20 may be modified to include additional, fewer, and/or different navigation controls from the navigation controls 50*a-f* shown in FIG. 2.

Figure 3:
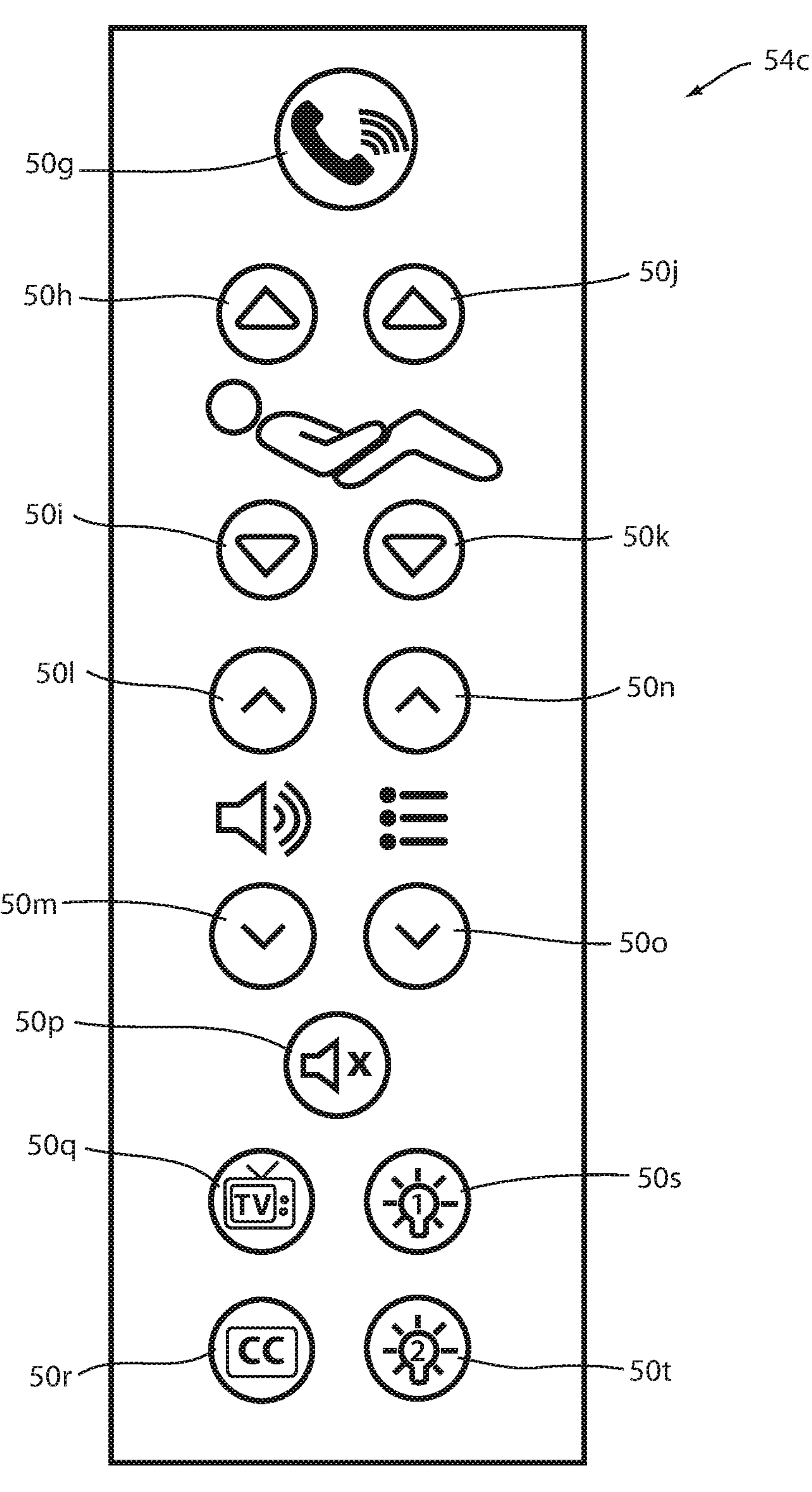
FIG. 3 is a plan view of an illustrative patient control panel of the patient support apparatus of FIG. 1.

FIG. 3 illustrates one example of a patient control panel 54*c* that may be incorporated into patient support apparatus 20 and positioned at a location on patient support apparatus 20 that is convenient for a patient to access while supported on support deck 30, such as on an interior side of one of the siderails 36. Control panel 54*c* includes a plurality of controls 50*g-t* that are intended to be operated by a patient. A nurse call control 50*g*, when pressed by the patient, sends a signal to a nurse call system requesting that a remotely positioned nurse talk to the patient. A Fowler-up control 50*h*, when pressed by the patient, causes a motorized actuator onboard patient support apparatus 20 to raise Fowler section 44 upwardly. A Fowler-down control 50*i*, when pressed by the patient, causes the motorized actuator to lower Fowler section 44 downwardly. A gatch-up control 50*j*, when pressed by the patient, causes another motorized actuator to raise a knee section of support deck 30, while a gatch-down control 50*k* causes the motorized actuator to lower the knee section of support deck 30. The knee section may refer to the joint that couples thigh section 46 to foot section 48.

A volume-up control 50*l*, when pressed by the patient, causes patient support apparatus to send a signal to an in-room television instructing it to increase its volume, while a volume down control 50*m*, when pressed, causes patient support apparatus 20 to send a signal to the television instructing it to decrease its volume. A channel-up control 50*n*, when pressed by the patient, causes patient support apparatus 20 to send a signal to the television instructing it to increase the channel number, while a channel-down control 50*o*, when pressed, causes patient support apparatus 20 to send a signal to the television instructing it to decrease the channel number.

A mute control 50*p*, when pressed, causes patient support apparatus 20 to send a signal to the television instructing it to either mute itself or unmute itself, depending upon whether the television is currently muted or unmuted. In other words, mute control 50*p* is a toggle control that alternatingly sends mute and unmute commands to the television when it is pressed.

Power control 50*q* is a toggle control that, when pressed, sends a signal to the television to either turn on or turn off, depending upon the television's current power status. Closed-captioning control is another toggle control that, when pressed, sends a signal to the television to either turn on its closed-captioning feature or to turn off its closed captioning feature, depending upon whether the closed-captioning feature is currently on or off.

Control 50*s* is a toggle control that, when pressed, sends a signal to a first light to either turn on or turn off, depending upon the current state of that first light. Control 50*t* is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54*c*, but also the functions of the controls 50 on control panel 54*c*, the layout of the controls 50 on control panel 54*c*, and/or other aspects of control panel 54*c* may be modified from what is shown in FIG. 3. In some embodiments, control panel 54*c* is implemented on a pendant controller that includes a cable that is plugged into a port on patient support apparatus 20. In other embodiments, one or more of the controls 50 of control panel 54*c* may be omitted, augmented, and/or split amongst other controls panels and/or locations. Still other manners of implementing control panel 54*c* are also possible.

Figure 4:
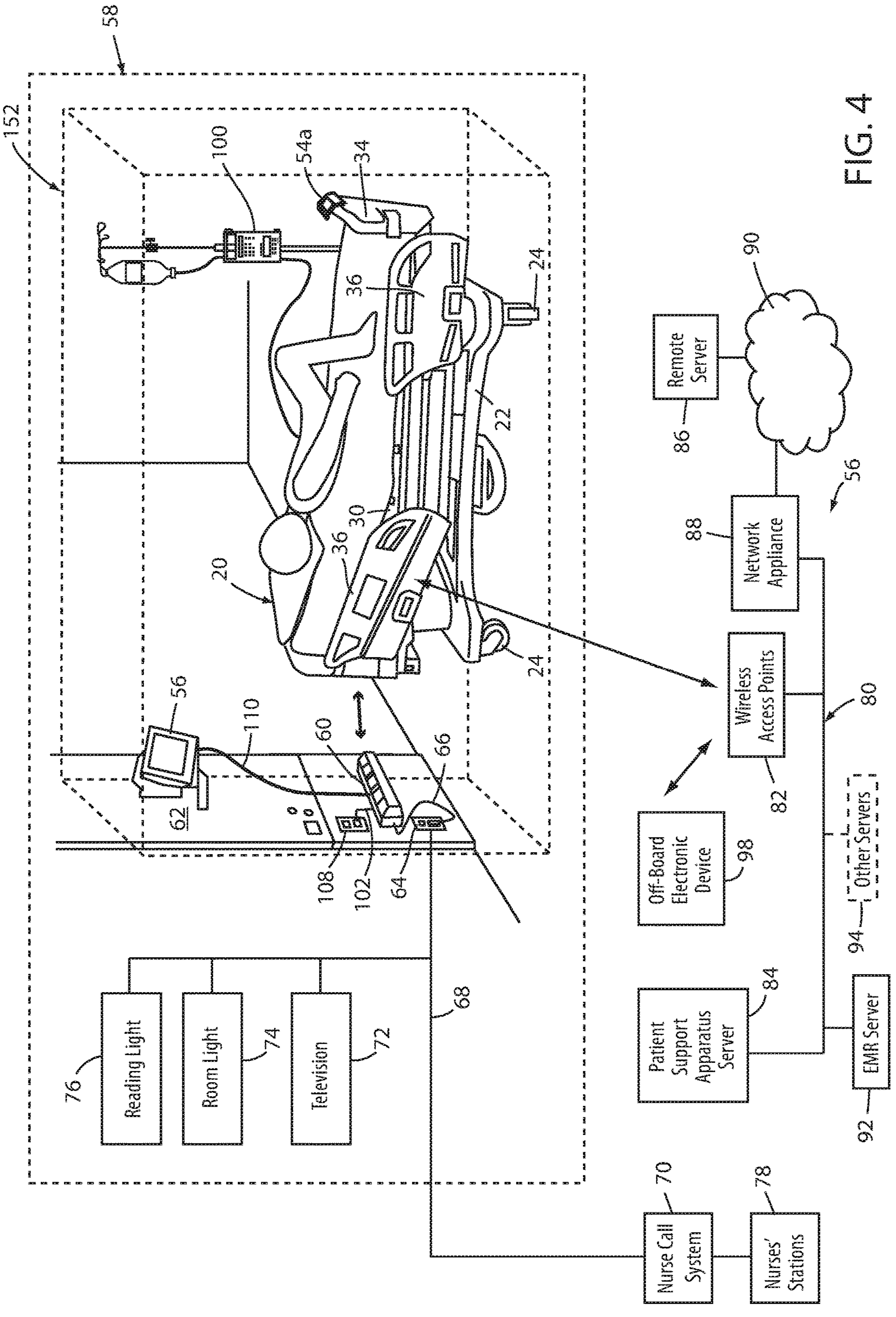
FIG. 4 is a perspective view of the patient support apparatus, an infusion pump, a display device, and a locator unit that is used for automatically detecting the location of a patient support apparatus.

FIG. 4 illustrates patient support apparatus 20 positioned within a room 58 of a healthcare facility. FIG. 4 also illustrates the additional items that may be present in a healthcare facility and which patient support apparatus 20 is configured to communicate with, including, but not limited to, a locator unit and a conventional local area network 80 of the healthcare facility. Locator units 60 are positioned at known and fixed locations within the healthcare facility in which patient support apparatus 20 is positioned. Locator units 60 function as fixed locators. That is, locator units 60 communicate with patient support apparatuses 20 and share information with them that allows the location of the patient support apparatuses to be determined.

In some embodiments, patient support apparatus 20 is configured to be able to communicate with at least two different types of locator units 60: linked locator units and unlinked locator units. One example of a linked locator unit 60 is shown in FIG. 4. One example of an unlinked locator unit is shown in FIG. 6 (unlinked locator unit 60*b*) of commonly assigned U.S. patent application Ser. No. 63/306,279 filed Feb. 3, 2022, by inventors Madhu Sandeep Thota et al. and entitled COMMUNICATION SYSTEM FOR PATIENT SUPPORT APPARATUSES, the complete disclosure of which is incorporated herein by reference. Patient support apparatus 20, in some embodiments, is configured to communicate with the unlinked locator units 60*b* described in the aforementioned '279 application and to perform any one or more of the functions described therein that utilize such unlinked locator units and/or information provided by such unlinked locator units.

Locator units 60 are communicatively linked to a conventional communication outlet 64 and are adapted to provide location information to patient support apparatus 20. Locator units 60 are also adapted to serve as a communication conduit for routing communications between patient support apparatus 20 and one or more devices and/or systems that are communicatively coupled to communication outlet 64 (e.g. room devices 72, 74, 76, and/or nurse call system 70, FIG. 4). In general, locator units 60 are typically positioned in patient rooms of the healthcare facility where one or more communication outlets 64 are typically present. Unless explicitly stated otherwise, references herein to "locator units 60" may refer to either linked or unlinked locator units 60.

As shown in FIG. 4, locator unit 60 is adapted to be mounted to a wall 62, such as a headwall of a patient room 58 within the healthcare facility. The headwall of a conventional healthcare facility room 58 typically includes a conventional communications outlet 64 physically integrated therein. Communications outlet 64 is adapted to receive a nurse call cable 66 that physically connects at its other end either to patient support apparatus 20 (not shown) or to locator unit 60 (shown in FIG. 4). In many healthcare facilities, communication outlet 64 includes a 37-pin connector, although other types of connectors are often found in certain healthcare facilities. As will be discussed in greater detail below, locator unit 60 and nurse call cable 66 allow patient support apparatus 20 to communicate with a nurse call system, and one or more room devices positioned within room 58.

Communication outlet 64 is electrically coupled to one or more cables, wires, or other conductors 68 that electrically couple the communication outlet 64 to a nurse call system 70 and one or more conventional room devices, such as a television 72, a room light 74, and/or a reading light 76. Conductors 68 are typically located behind wall 62 and not visible. In some healthcare facilities, conductors 68 may first couple to a room interface circuit board that includes one or more conductors 68 for electrically coupling the room interface circuit board to room device 72, 74, 76 and/or nurse call system 70. Still other communicative arrangements for coupling communication outlet 64 to nurse call system 70 and/or one or more room devices 72, 74, 76 are possible.

Nurse call cable 66 (FIG. 4) enables locator unit 60 to communicate with nurse call system 70 and/or room devices 72, 74, 76, and because patient support apparatus 20 is able to wirelessly communicate with locator unit 60, patient support apparatus 20 is thereby able to communicate with nurse call system 70 and room devices 72, 74, 76. A patient supported on patient support apparatus 20 who activates a nurse call control (e.g. 50*g*; see FIG. 3) on patient support apparatus 20 causes a signal to be wirelessly sent from patient support apparatus 20 to locator unit 60, which in turn conveys the signal via nurse call cable 66 to the nurse call system 70, which forwards the signal to one or more remotely located nurses (e.g. nurses at one or more nurse's stations 78). If the patient activates one or more room device controls (e.g. controls 50*l-t*; see FIG. 3), one or more wireless signals are conveyed to locator unit 60, which in turn sends appropriate signals via nurse call cable 66 to communication outlet 64 and the room device 72, 74, 76 that change one or more features of these devices (e.g. the volume, channel, on/off state, etc.).

As is also shown in FIG. 4, patient support apparatus 20 is further configured to communicate with a local area network 80 of the healthcare facility. In the embodiment shown in FIG. 4, patient support apparatus 20 includes a wireless network transceiver 96 (FIG. 5) that communicates wirelessly with local area network 80. Network transceiver 96 is, in at least some embodiments, a WiFi transceiver (e.g. IEEE 802.11) that wirelessly communicates with one or more conventional wireless access points 82 of local area network 80. In other embodiments, network transceiver 96 may be a wireless transceiver that uses conventional 5G technology to communicate with network 80, one or more servers hosted thereon, and/or other devices. In some embodiments, network transceiver 96 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 96 is a wired transceiver that is adapted to allow patient support apparatus 20 to communicate with network 80 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 96 for communicating with network 80 via a wired connection and a wireless transceiver 96 for wirelessly communicating with network 80.

Patient support apparatus 20 is configured to communicate with one or more servers on local area network 80 of the healthcare facility. One such server is a patient support apparatus server 84. Patient support apparatus server 84 is adapted, in at least one embodiment, to receive status information from patient support apparatuses 20 positioned within the healthcare facility and distribute this status information to caregivers, other servers, and/or other software applications. As will be discussed in greater detail below, server 84 may also be configured to receive data from one or more medical devices that are positioned within a volume of space defined around patient support apparatus 20 and/or within a volume of space defined around locator units 60. In some embodiments where data from medical devices is collected, the data from one or more of the medical devices may be forwarded to an Electronic Medical Records (EMR) server 92, and/or to one or more other servers 94 on network 80 (and/or one or more electronic devices 98), such as a caregiver assistance server and/or a caregiver assistance software application, as will also be discussed in greater detail below.

In some embodiments, patient support apparatus server 84 is configured to communicate at least some of the patient support apparatus status data and/or medical device data received from patient support apparatuses 20 to a remote server 86 that is positioned geographically remotely from the healthcare facility. Such communication may take place via a conventional network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

In some alternative embodiments, patient support apparatus 20 may be configured to communicate directly with one or more cloud-based servers, such as remote server 86, without utilizing patient support apparatus server 84. That is, in some embodiments, patient support apparatuses 20 may be configured to communicate directly with a remote server without relying upon any locally hosted servers (e.g. servers hosted on network 80). In one such embodiment, patient support apparatus 20 utilizes Microsoft's Azure cloud computing service to directly connect to one or more remote servers 86 without utilizing server 84. In some such embodiments, network appliance 88 is a router configured to support such direct connections. Still other types of direct-to-cloud connections may be utilized with one or more of patient support apparatuses 20.

Patient support apparatus server 84 is also configured to determine the location of each patient support apparatus 20, or receive the location of each patient support apparatus 20 from the patient support apparatuses 20. In some embodiments, patient support apparatus server 84 determines the room number and/or bay area of each patient support apparatus 20 that is positioned within a room 58, as well as the location of patient support apparatuses 20 that are positioned outside of a room 58, such as, those that may be positioned in a hallway, a maintenance area, or some other area. In general, patient support apparatus server 84 may be configured to determine the position of any patient support apparatus 20 that is positioned within communication range of one or more locator units 60, as will be discussed in greater detail below. Still further, patient support apparatus server 84 may be configured to receive an HL-7 feed from EMR server 92 of one or more pieces of medical information pertaining to patients assigned to specific patient support apparatuses.

As will be discussed in greater detail below, patient support apparatus server 84, in conjunction with patient support apparatus 20, may be configured to double-check the amount and/or rate of medication that is being delivered to a patient from an infusion pump 100, and to alert a caregiver if one or both of them detect a medication level that is too high. Such double-checking may be carried out through communications with a conventional EMR server 92 that is typically present in any healthcare facility. Patient support apparatus server 84 is adapted to communicate with EMR server 92 in order to exchange data therewith. In some embodiments, server 84 communicates with EMR server 92 in order to transmit patient data that is to be recorded in a patient's health record (e.g. vital sign readings from one or more vital sign sensors; weight readings taken from the scales built into patient support apparatuses 20; therapies provided to patients using a powered mattress 42 onboard patient support apparatuses 20; data from other medical devices that are determined to be associated with the patient assigned to patient support apparatus 20, etc.). In addition, server 84 communicates with EMR server 92, in some embodiments, in order to receive data from one or more infusion pumps 100 that are being used to deliver medication to a patient.

It will be understood that the architecture and content of local area network 80 will vary from healthcare facility to healthcare facility, and that the example shown in FIG. 4 is merely one example of the type of network a healthcare facility may be employ. Typically, one or more additional servers 94 will be hosted on network 80 and one or more of them may be adapted to communicate with patient support apparatus server 84. Local area network 80 will also typically allow one or more electronic devices 98 to access the local area network 80 via wireless access points 82. Such electronic devices 98 include, but are not limited to, smart phones, tablet computers, portable laptops, desktop computers, smart televisions, and other types of electronic devices that include a WiFi capability and that are provided with the proper credentials (e.g. SSID, password, etc.) to access network 80 (and, in at least some situations, patient support apparatus server 84). As will be discussed in further detail herein, patient support apparatus server 84 is configured, in some embodiments, to share data with one or more electronic devices 98 that relates to patient support apparatus 20, that relates to one or more medical devices that are associated with patient support apparatus 20 (or the patient assigned thereto), and/or that relates to one or more medical records of the patient stored in EMR server 92.

Locator units 60 are adapted to wirelessly receive signals from patient support apparatus 20 and deliver the signals to communications outlet 64 in a manner that matches the way the signals would otherwise be delivered to communications outlet 64 if a conventional nurse call cable 66 were connected directly between patient support apparatus 20 and communications outlet 64. Locator units 60 are also adapted to transmit signals received from communications outlet 64 to patient support apparatus 20 via a BT transceiver 106 and/or a UWB transceiver 104 (FIG. 5). Thus, patient support apparatus 20 and locator unit 60 cooperate to send signals to, and receive signals from, communications outlet 64 in a manner that is transparent to communications outlet 64 such that outlet 64 cannot detect whether it is in communication with patient support apparatus 20 via a wired connection or it is in communication with patient support apparatus 20 via a wireless connection between patient support apparatus 20 and locator unit 60 (the latter of which is in wired communication with outlet 64). In this manner, a healthcare facility can utilize the wireless communication abilities of one or more patient support apparatuses 20 without having to make any changes to their existing communication outlets 64.

As noted, in addition to sending signals received from patient support apparatus 20 to communications outlet 64, locator units 60 are also adapted to forward signals received from communications outlet 64 to patient support apparatus 20. Locator units 60 are therefore adapted to provide bidirectional communication between patient support apparatus 20 and communications outlet 64. This bidirectional communication includes, but is not limited to, communicating command signals from any of controls 50 and/or from any of electronic devices 98 to corresponding room devices 72, 74, and/or 76 and communicating audio signals between a person supported on patient support apparatus 20 and a caregiver positioned remotely from patient support apparatus 20. The audio signals received by locator units 60 from a microphone on patient support apparatus 20 are forwarded to communications outlet 64 (for forwarding to nurse call system 70), and the audio signals of a remotely positioned nurse that are received at communications outlet 64 (from nurse call system 70) are forwarded to a speaker onboard patient support apparatus 20.

Nurse call cable 66, in some embodiments, includes a conventional 37 pin connector on each end, one of which is adapted to be inserted into outlet 64 and the other one of which is adapted to be inserted into locator unit 60. Such 37 pin connections are one of the most common types of connectors found on existing walls of medical facilities for making connections to the nurse call system 70 and room devices 72, 74, and 76. Locator unit 60 and nurse call cable 66 are therefore configured to mate with one of the most common type of communication outlets 64 used in medical facilities. Such 37 pin connectors, however, are not the only type of connectors, and it will be understood that locator units 60 can utilize different types of connectors that are adapted to electrically couple to different types of nurse call cables 66 and/or different types of communication outlets 64. One example of such an alternative communications outlet 64 and cable 66 is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors may be utilized.

Locator unit 60 (FIG. 4) also includes an electrical cord 102 having a plug positioned at a far end that is adapted to be inserted into a conventional electrical outlet 108. Electrical cord 102 enables locator unit 60 to receive power from the mains electrical supply via outlet 108. It will be appreciated that, in some embodiments, locator unit 60 is battery operated and cord 102 may be omitted. In still other embodiments, locator unit 60 may be both battery operated and include cord 102 so that in the event of a power failure, battery power supplies power to locator unit 60, and/or in the event of a battery failure, electrical power is received through outlet 108.

In some embodiments, locator units 60 include a video port that is adapted to receive a display cable 110 (FIG. 4). The display cable 110 is adapted to couple to locator unit 60 at one end and a display device 56 at its opposite send. Locator unit 60 may be configured to use cable 110 send data to display device 56 that is to be displayed thereon. Such data may include data from one or more medical devices (e.g. infusion pump 100, one or more vital sign sensors, and/or other types of medical devices) that are associated with the patient on patient support apparatus 20 (or with patient support apparatus 20 itself), status data from one or more sensors onboard patient support apparatus 20, location data regarding the location of patient support apparatus 20, and/or other data. Cable 110 may be a High-Definition Multimedia Interface (HDMI) cable, a Video Graphics Array (VGA) cable, a DisplayPort (DP) cable, a plurality of Radio Corporation of America (RCA) cables, a Digital Visual Interface (DVI) cable, and/or another type of cable. Locator unit 60 is configured to include a complementary type of connector that mates with a connector on an end of cable 110. Further details regarding the communication between patient support apparatus 20 and display device 56 are provided below and, in some embodiments, patient support apparatus 20 may be configured to communicate directly with certain display devices without using locator unit 60 as a communication intermediary.

In addition to any of the structures and functions described herein, locator units 60 are configured to communicate location data to patient support apparatus 20 that enables patient support apparatus 20 and/or patient support apparatus server 84 to determine the location of patient support apparatus 20 within the healthcare facility. In general, such location determination is carried out by patient support apparatus 20 analyzing wireless signals communicated between itself and locator unit 60 to determine its position relative to locator unit 60. After determining its relative position to locator unit 60, patient support apparatus 20 is configured to be able to have its absolute position within the healthcare facility determined by receiving a unique locator identifier (ID) 122 (FIG. 5) from the locator unit 60. The location of each locator unit 60 in the healthcare facility is surveyed during the installation of locator units 60, and the unique IDs 122 of each locator unit 60 are also recorded during the installation of locator units 60. This surveying information and corresponding ID information may be stored in patient support apparatus server 84 and/or onboard patient support apparatus 20, thereby enabling patient support apparatus 20 and/or patient support apparatus server 84 to determine the location of a patient support apparatus 20 once its relative position to an identified locator unit 60 is known.

If the location of patient support apparatus 20 is determined remotely, patient support apparatus 20 sends its relative position information and the ID 122 of the locator unit 60 (and its own unique patient support apparatus ID 130 (FIG. 5)) to server 84. Server 84 includes a table of all of the locations of the locator units 60 (which, as noted, is generated via a surveying operation during the installation of locator units 60), and it uses that table to correlate the patient support apparatus IDs 130 and the locator unit IDs 122 it receives to specific locations within the healthcare facility. Thus, if a particular patient support apparatus 20 (with a particular ID 130) sends a locator unit ID 122 that corresponds to room 430, server 84 determines that that particular patient support apparatus 20 is currently located in room 430. Generally speaking, and as will be discussed in greater detail below, the location of a patient support apparatus 20 is deemed to correspond to whichever locator unit 60 it is currently associated with, and if it is not currently associated with any locator unit 60, its location may be indeterminate.

In some embodiments of patient support apparatus 20 and locator unit 60, the relative location of patient support apparatus 20 to a locator unit 60 is carried out solely using ultra-wideband communication between the patient support apparatus 20 and the locator unit 60. Alternatively, in some embodiments, patient support apparatus 20 solely uses short range infrared communications with locator unit 60 to determine its relative location, wherein such short range infrared communications are only possible when the patient support apparatus 20 is positioned within a close proximity to the locator unit 60 (e.g. in the range of about 1-3 unobstructed meters). In these latter embodiments, patient support apparatus 20 may report that its location coincides with that of the nearby locator unit 60 when it is able to successfully communicate with the nearby locator unit 60 using these short range infrared communications. Still further, in some embodiments, patient support apparatus 20 and locator units 60 may communicate with each other using both infrared and ultra-wideband communications. Further details regarding the use of short range infrared communications for location determination are described in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

In some embodiments, locator units 60 and/or patient support apparatuses 20 may be constructed to include any or all of the functionality of the wireless headwall units and/or patient support apparatuses disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; in commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION; and/or in commonly assigned U.S. patent application Ser. No. 63/245,245 filed Sep. 17, 2021, by inventors Kirby Neihouser et al. and entitled SYSTEM FOR LOCATING PATIENT SUPPORT APPARATUSES, the complete disclosures of all of which are incorporated herein by reference.

Still further, in some embodiments, locator units 60 and/or patient support apparatuses 20 may be constructed to include any of the features and/or functions of the headwall units 144*a* and/or patient support apparatuses disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

FIG. 5 depicts a block diagram of patient support apparatus 20, a locator unit 60, an infusion pump 100, a vital sign sensor 150, a display device 56, and network 80. As will be discussed in greater detail below, patient support apparatus 20 is configured to automatically determine the location of one or more infusion pumps 100. In addition, in some embodiments, patient support apparatus 20 is further configured to automatically determine the position of one or more locator units 60 and/or one or more other types of medical devices, such as, but not limited to, one or more vital sign sensors. In addition, patient support apparatus 20 is configured to automatically carry out communications with those devices if they are positioned within a defined proximity to patient support apparatus 20. In some embodiments, if the device is positioned within the defined proximity, patient support apparatus 20 automatically associates the device with the patient assigned to patient support apparatus 20 (and/or with patient support apparatus 20 itself), and causes data from that device (or devices) to be displayed on one or more of display devices 56, and/or forwards data from that device (or devices) to patient support apparatus server 84 and/or EMR server 92 in communication with network 80. Alternatively, or additionally, patient support apparatus 20, in conjunction with patient support apparatus server 84, automatically retrieves data from EMR server 92 regarding the data that the medical device(s) (e.g. infusion pump 100, vital signs sensors 150, etc.) are sending to EMR server 92 and performs one or more analyses of that data, such as, but not limited to, double checking the amount of medication being delivered to the patient.

Locator unit 60 includes an ultra-wideband transceiver 104, a Bluetooth transceiver 106, a locator unit controller 112, configuration circuitry 114, a television controller 116, a headwall interface 118, a video port 120, a unit ID 122, and, in some embodiments, an infrared transceiver 124. Bluetooth transceiver 106 is adapted to communicate with a Bluetooth transceiver 128 onboard patient support apparatus 20 using RF waves in accordance with the conventional Bluetooth standard (e.g. IEEE 802.14.1 and/or the standard maintained by the Bluetooth Special Interest Group (SIG) of Kirkland, Washington, USA). In some embodiments, transceivers 106 and 128 utilize Bluetooth Low Energy communications.

Ultra-wideband transceiver 104 is adapted to communicate with one or more ultra-wideband transceivers 132 positioned onboard patient support apparatus 20. Transceiver 104 is adapted to determine a distance between itself and patient support apparatus 20. Alternatively, or additionally, transceiver 104 may be adapted to allow one or more of the UWB transceivers 132 onboard patient support apparatus 20 to determine their distance from transceiver 104. In some embodiments, transceivers 104 and 132 use time of flight (TOF) computations to determine these distances. In other embodiments, transceiver 104 and 132 may utilize other techniques for determining their distances from each other, either in addition to, or in lieu of, TOF computations. In some embodiments, transceivers 104, 132 may also determine an angle between themselves using angular information derived from antenna arrays positions onboard transceivers 104, 132, or by using other techniques. The position and orientation of each transceiver 132 onboard patient support apparatus 20 is known and stored in an onboard memory 134 and used to determine the position and orientation of patient support apparatus 20 with respect to the locator unit(s) 60 with which it is communicating.

In some embodiments, transceivers 104, 132 are implemented as any of the Trimension™ ultra-wideband modules available from NXP Semiconductors of Austin, Texas. These modules include, but are not limited to, the Trimension™ UWB modules ASMOP1BO0N1, ASMOP1CO0R1, and/or the ASMOP1CO0A1, that utilize any of the following chips: the NXP SR150, SR100T, SR040, NCJ29D5, and/or the 0L23D0 chips. Modules manufactured and/or marketed by other companies may also be used, including, but not limited to, the Decawave DWM1000, DWM10001C, DWM3000 modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB modules may be used to implement transceivers 104 and 132.

Locator unit controller 112 is adapted to control the operation of transceivers 104, 106, configuration circuitry 114, TV controller 116, headwall interface 118, video port 120, and, if included, IR transceiver 124 (FIG. 5). When infrared transceiver 124 is included, it may be included to provide backwards compatibility to patient support apparatuses 20 that are not equipped with a UWB transceiver 132. That is, some healthcare facilities may include one or more patient support apparatuses that are not equipped with a UWB transceiver 132, but that do include an IR transceiver that is adapted to communicate with IR transceiver 124. When locator unit 60 includes IR transceiver 124, it is able to communicate its unit ID 122 to such patient support apparatuses via IR transceiver 124, which is a short range transceiver that is configured to only communicate with an adjacent patient support apparatus when the patient support apparatus is nearby (e.g. without about five feet or so). Such an adjacent patient support apparatus 20 then communicates the received locator unit ID 122 along with its own unique ID 130 (FIG. 5) to server 84 which, as noted previously, is able to correlate the locator unit ID 122 to a particular location with the healthcare facility. In this manner, server 84 is able to use locator units 60 determine the location of versions of patient support apparatuses 20 that don't have a UWB transceiver 132, but that do have an IR transceiver.

Headwall interface 118 is adapted to change the electrical state of one or more pins that are in electrical communication with communication outlet 64 (via cable 66). Headwall interface 118 changes these electrical states in response to instructions from controller 112. For example, if the exit detection system 136 of patient support apparatus 20 detects a patient exit, a controller 140 of patient support apparatus 20 sends an exit alert signal to locator unit 60 and controller 112 responds by instructing headwall interface 118 to change the electrical state of at least one pin that is used to signal an exit alert (or a generic priority alert) to the nurse call system 70 via communications outlet 64. In some embodiments, headwall interface 118 may be constructed in the same manner as, and/or may include any one or of the functions as, the cable interface 88 described in commonly assigned U.S. patent application Ser. No. 63/193,778 filed May 27, 2021, by inventors Krishna Bhimavarapu et al. and entitled PATIENT SUPPORT APPARATUS AND HEADWALL UNIT SYNCING, the complete disclosure of which is incorporated herein by reference. Alternatively, or additionally, headwall interface 118 may be constructed in the same manner as, and/or may include any one or more of the same functions as, the headwall interface 120 disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference. Locator unit 60 may also be configured to perform any of the functions of the headwall units 94 disclosed in the above-mentioned '778 patent application.

Configuration circuitry 114 and TV controller 116 may be configured to perform any of the same functions as, and/or be constructed in any of the same manners as, the configuration circuitry 132 and the TV control circuit 134, respectively, of commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which has already been incorporated herein by reference. Additionally, or alternatively, locator unit 60 may be configured to perform any of the functions of the headwall units 144 disclosed in the aforementioned '508 patent application.

Patient support apparatus 20 includes a controller 140, a memory 134, exit detection system 136, a microphone 142, Bluetooth transceiver 128, one or more UWB transceivers 132, display 52 (which may be part of control panel 54*a*, and/or another control panel 54), network transceiver 96, and a plurality of additional components that are not shown in FIG. 5. Each UWB transceiver 132 is positioned at a known location on patient support apparatus 20. This known location information is stored in memory 134 and/or elsewhere, and may be defined with respect to any suitable frame of reference that is common to patient support apparatus 20. The known location information may include the spatial relationship between UWB transceivers 132 and/or any other components of patient support apparatus 20. For example, in some embodiments, the known location information includes the spatial relationship not only between UWB transceivers 132, but also the spatial relationships between UWB transceivers 132 and one or more of the following: the head end 38 of patient support apparatus 20, the foot end of patient support apparatus 20, the sides of patient support apparatus 20, the floor, and/or other components and/or landmarks of patient support apparatus 20. In some embodiments, this location information is used to determine the orientation of patient support apparatus 20 with respect to one or more walls 62, locator units 60, another patient support apparatus 20, and/or another object or structure within the healthcare facility.

In some embodiments, patient support apparatus 20 includes four UWB transceivers 132, each of which are position generally adjacent one of the four corners of patient support apparatus 20. In some such embodiments, the four UWB transceiver 132 are attached to, or positioned near, the four corners of litter frame 28. In other embodiments, the four UWB transceivers 132 are attached to, or positioned near, the four corners of base 22. In some embodiments, each of the four UWB transceivers 132 are attached to the corners of support deck 30. Still other locations of the UWB transceivers 132, as well as different numbers of the UWB transceiver 132, may be incorporated into patient support apparatus 20. In those embodiments of patient support apparatus 20 where one or more of the UWB transceiver 132 are coupled to components of patient support apparatus 20 that are movable (e.g. litter frame 28, which can have its height and orientation changed; or support deck 30 that can have its sections, such as head section 44, pivoted), sensors are included within patient support apparatus 20 that communicate the current position of the UWB transceivers 132 to controller 140 so that controller 140 is able to use the current position information of the UWB transceivers 132 when determining the current location of an infusion pump 100, another type of medical device, and/or a locator unit 60.

Controller 140, as well as controller 112, may take on a variety of different forms. In the illustrated embodiment, each of these controllers is implemented as a conventional microcontroller. However, these controllers may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 112 and 140 when carrying out the functions described herein, as well as the data necessary for carrying out these functions, are stored in a corresponding memory that is accessible to that particular controller (e.g. memory 134 for controller 140, and a memory (not shown) for controller 112). In some embodiments, controller 140 may include and/or work with a microcontroller that is integrated into, or associated with, UWB transceiver(s) 132, and controller 112 may include and/or work with a microcontroller that is integrated into, or associated with, UWB transceiver 104.

Controller 140 utilizes UWB transceivers 132 to determine the relative position of patient support apparatus 20 with respect to one or more nearby locator units 60 and/or to determine the relative position of infusion pump 100 (and/or other medical devices) to patient support apparatus 20. If patient support apparatus 20 is positioned within range of a locator unit 60, its UWB transceivers 132 communicate with the UWB transceiver 104 positioned on that locator unit 60, and the transceivers 132 and 104 exchange signals that enable them to determine the distances between themselves. This distance determination is done for each UWB transceiver 132 positioned onboard patient support apparatus 20 (or for as many as is necessary in order to determine an accurate position of locator unit 60 relative to patient support apparatus 20).

In some embodiments, UWB transceivers 104, 132 may also be configured to determine an angular relationships between themselves. The distance (and angle information) in at least some embodiments is calculated by UWB transceiver 132 and controller 140 of patient support apparatus 20. In other embodiments, UWB transceiver 104 and controller 112 may calculate the distance (and angle information) and forward the results of this calculation to patient support apparatus 20 (either via UWB transceiver 104 or BT transceiver 106). In either situation, patient support apparatus controller 140 is informed of the distances (and, in some embodiments, as noted, the angle information) between transceivers 132 and 104. These distances and orientations are then used to calculate a relative position of patient support apparatus 20 to the locator unit 60 in a common frame of reference that may be defined in a fixed relationship to the patient support apparatus 20 or in a fixed relationship to the locator unit 60.

Although FIGS. 4 and 5 only illustrate a single locator unit 60, it will be understood that a typical healthcare facility will include multiple locator units 60 positioned at different locations throughout the facility, including ones positioned within patient rooms and others positioned outside of patient rooms. Typically, at least one locator unit 60 will be positioned in each patient room of the healthcare facility, and if the patient room is intended to be occupied by more than one patient (e.g. it includes multiple bays), then additional locator units 60 may be included so that each patient support apparatus 20 will have a locator unit 60 positioned adjacent to each bay area in the room. Additional locator units 60, such as unlinked locator units 60, may also be positioned at other locations through the healthcare facility.

The location of patient support apparatus 20 relative to locator units 60 is repetitively determined by an exchange of communication signals between UWB transceivers 104 and 132. This exchange is initiated by an interrogation signal that may be sent by the UWB transceivers 104 of the locator unit 60, and/or it may be sent by the UWB transceivers 132 of the patient support apparatuses 20. The trigger for sending these interrogation signals (from either source) may simply be the passage of a predefined interval of time, in at least some embodiments. That is, in some embodiments, patient support apparatus 20 and/or locator units 60 may be configured to periodically send out an interrogation signal that will be responded to by any UWB transceivers 104 or 132 that are positioned with range of that signal. In those embodiments where patient support apparatuses 20 are configured to send out such an interrogation signal, the time intervals between the interrogation signals may be varied depending upon the location and/or other status of the patient support apparatus 20. For example, in some embodiments, patient support apparatuses 20 may be configured to send out the interrogation signals with longer timer intervals between them when the patient support apparatus is stationary, and to send out the interrogation signals with shorter time intervals between them when the patient support apparatus 20 is in motion. Indeed, in some embodiments, after patient support apparatus 20 has ceased moving, controller 140 may be configured to cease sending out such interrogation signals until it once again starts moving. In any of the aforementioned embodiments, motion of the patient support apparatus 20 may be detected in any suitable manner, such as by including one or more motion sensors on the patient support apparatus 20 (e.g. one or more accelerometers), and/or by monitoring the values of the repetitive distance measurements and looking for changes indicative of movement.

The measured distances (and/or angular information between locator units 60 and patient support apparatuses 20) that are generated from the communications between UWB transceivers 104, 132 may utilize Angle of Arrival (AoA) information, Time of Flight (TOF) information, Channel State Information, Time Difference of Arrival (TDoA) information, Two-Way Ranging (TWR) ranging information, and/or other information. In some embodiments, each transceiver 104, 132 includes an array of antennas that are used to generate distance and/or angular information with respect to the transceivers 104, 132 in which it is in communication. Still further, in some embodiments, transceivers 104, 132 include one or more of their own microcontrollers, and the location of transceivers 104, 132 may be determined by these internal microcontrollers without utilizing controller 140 and/or 112. In other embodiments, controllers 112 and/or 140 may work in conjunction with the microcontrollers of transceivers 104, 132 to determine their relative locations to each other.

Patient support apparatus 20 also includes, in at least some embodiments, a microphone 142 (FIG. 5) that is used to detect the voice of the patient when the patient wants to speak to a remotely positioned nurse. The patient's voice is converted to audio signals by microphone 142 and controller 140 is adapted to forward these audio signals to an adjacent communications outlet 64 positioned in wall 62 (FIG. 4). When a cable 66 is coupled between patient support apparatus 20 and outlet 64, controller 140 forwards these audio signals to outlet 64 via the cable. When no such cable 66 extends between patient support apparatus 20 and outlet 64, controller 140 wirelessly forwards these audio signals to the locator unit 60 that it is currently associated with (using transceiver 128, or in some embodiments, one of transceivers 132) and controller 112 of locator unit 60 forwards these audio signals to outlet 64. As was noted, outlet 64 is in electrical communication with a conventional nurse call system 70 that is adapted to route the audio signals to the correct nurse's station 78, and/or other location. In some embodiments, microphone 142 acts as both a microphone and a speaker. In other embodiments, a separate speaker may be included in order to communicate the voice signals received from the remotely positioned nurse. In some embodiments, the audio communication between patient support apparatus 20 and communications outlet 64 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

After the installation of locator units 60 in a particular healthcare facility, the location of each locator unit 60 within that facility is recorded. In some embodiments, the coordinates of the locations of locator units 60 are recorded in a common frame of reference (or converted to a common frame of reference after recordation). Such coordinates may be three dimensional (i.e. include a height components), or they may be two dimensional (no height component). In other embodiments, a more generalized location of one or more locator units 60 is determined, rather than the precise coordinates of the locator units 60. In still other embodiments, the locations of one or more locator units 60 are determined both generally and more precisely. The generalized location of the locator units 60 may include an indication of the room, bay, area, hallway, portion of a hallway, wing, maintenance area, etc. that the locator unit 60 is positioned in. The specific location of the locator units 60, as noted, may include an X, Y, and Z coordinate within a common frame of reference.

Regardless of how the location of each locator unit 60 is initially determined after they are installed in a healthcare facility (e.g. whether their coordinates are determined or a more generalized location is determined), the locations of all of the locator units 60, as well as their unique IDs 122, are stored in a memory accessible to server 84. Server 84 then uses this location data and ID data to determine the location of a patient support apparatus 20. Alternatively, or additionally, the location data and ID's 122 are forwarded to patient support apparatuses 20 for storage in their onboard memories 134 and for use in determining their own locations. In some embodiments, the location of each locator unit 60 (whether specific and/or general) may also, or alternatively, be stored in a memory within that particular locator unit 60 and shared with the devices it communicates with (e.g. patient support apparatuses 20). In some other embodiments, the location of each locator unit 60 may be stored in multiple locations.

It will be appreciated that patient support apparatuses 20 are configured to communicate with locator units 60 regardless of the orientation of the patient support apparatus 20. That is, the UWB transceivers 104 and 132 are radio frequency transceivers that do not rely on line of sight communication, unlike the IR transceiver 124 (if present). Thus, the patient support apparatuses 20 do not have to be pointed in any particular direction with respect to the locator units in order for transceivers 104 and 132 to communicate. This differs from some prior art systems that use IR communication between the patient support apparatuses 20 and the locator units and that require the IR transceiver onboard the patient support apparatus to be aimed toward the locator unit in order for communication to be established. It will also be understood that locator units 60 can be positioned on wall, columns, ceilings, or any other fixed structures within the healthcare facility.

Patient support apparatus 20 is also configured to use UWB transceivers 132 to determine the position of various other devices relative to patient support apparatus 20, such as one or more infusion pumps 100, one or more vital sign sensors 150, and/or one or more other types of devices that are physically separated from patient support apparatuses 20 (FIG. 5). As will be discussed in greater detail below, controller 140 uses UWB transceivers 132 to determine the relative position of these devices by communicating with one or more respective UWB transceivers that are either built into those devices or attached to a tag that is affixed to those devices. Such UWB transceivers operate in the same manner as UWB transceivers 132 and/or UWB transceiver 104 of locator units 60. And, as will also be discussed in greater detail below, controller 140 of patient support apparatus 20 uses the relative position information to determine how it will interact with these devices, including whether to associate with these devices or not. When controller 140 associates patient support apparatus 20 with one or more of these devices, as will be discussed in greater detail below, controller 140 and/or server 84 may take one or more of the following actions: display data from these devices on display 52 and/or display device 56, send data from one or more of these devices to patient support apparatus server 84 and/or EMR server 92 on network 80, send a patient weight to the devices (e.g. one or more infusion pumps 100), retrieve data from EMR server 92 that was generated by these devices, retrieve data from these devices via another route that is independent from EMR server 92, and/or take other actions.

Vital sign sensor 150 (FIG. 5) includes a UWB transceiver 146, a controller 148, one or more vital sign transducers 144, and a unique ID 154. UWB transceiver 146 is adapted to communicate with the UWB transceivers 132 positioned onboard patient support apparatus 20 so that the position of vital sign sensor 150 relative to patient support apparatus 20 can be repetitively determined. UWB transceiver 146 may be the same as all of the other UWB transceivers discussed herein (e.g. UWB transceivers 132, 104, etc.). UWB transceiver 146 is further adapted to transmit the unique ID 154 of vital sign sensor 150 to patient support apparatus 20 so that patient support apparatus 20 knows which specific vital sign sensor it is communicating with. As will be discussed in greater detail below, controller 140 may forward this vital sign ID 154 to patient support apparatus server 84 and server 84 may use the ID for one or more purposes, such as, but not limited to, communicating with EMR server 92, communicating with one or more electronic devices 98, and/or for other purposes.

Controller 148 of vital sign sensor 150 is adapted to oversee the operation of vital sign sensor 150, process the communications of UWB transceiver 146 with other UWB transceivers (e.g. transceivers 132), and process the outputs of vital sign transducer 144. Controller 162 may further be adapted, in some embodiments, to forward vital sign data to EMR server 92 via a network transceiver (not shown) coupled to access points 82. In such embodiments, the forwarded vital sign data may then become available to various servers on network 80, such as patient support apparatus server 84, via an HL-7 feed. Alternatively, vital sign controller 148 may be configured without the ability to forward data to network 80 via access points 82.

Vital sign transducer 144 may vary from vital sign sensor 150 to vital sign sensor 150. In some embodiments, where vital sign sensor 150 is adapted to detect a patient's blood pressure, vital sign transducer 144 may be a pressure sensor adapted to detect the pressure of the patient's blood. For other vital sign sensors 150, transducer 144 may be a thermometer for measuring the patient's temperature, a pressure or sound detector for measuring the patient's breathing rate, a sound detector for measuring the patient's heart rate, an infrared light detector for detecting reflected infrared light in a pulse oximeter, and/or any other type of transducer, sensor, or detector that is capable of detecting one or more vital signs, or other medically significant characteristics of the patient.

Controller 148 of vital sign sensor 150 may comprise a microcontroller and/or any of the other structures that were mentioned above and that comprise controller 140 and/or controller 112. Controller 148 is adapted to send vital signs readings derived from the transducer 144 to patient support apparatus 20 when the vital sign sensor 150 is associated with the patient support apparatus 20. As will be discussed in more detail below, controller 140 of patient support apparatus 20 decides whether to associate a particular device, such as a vital sign sensor 150, with patient support apparatus 20 (or the patient assigned to patient support apparatus 20) if it is currently positioned in a predefined location. In general, controller 140 associates devices, such as vital sign sensor 150 and/or infusion pumps 100, with patient support apparatus 20 if the device is positioned within a predetermined volume of space 152 (FIG. 4) that is defined around, and with respect to, patient support apparatus 20.

If controller 140 of patient support apparatus 20 concludes that a vital sign sensor 150 is currently positioned within predetermined space volume 152, and therefore associates that particular vital sign sensor 150 with patient support apparatus 20, controller 140 is configured to request and/or receive vital sign data from the vital sign sensor 150. Additionally, controller 140 is configured to forward that vital sign data to one or more recipients, such as a locator unit 60 (which may then forward it to display device 56 for display thereon), one or more displays 52 positioned onboard patient support apparatus 20, and/or one or more servers on the local area network 80 of the healthcare facility. When forwarding the vital sign data from patient support apparatus 20 to a locator unit 60, controller 140 may utilize BT transceiver 128 to send the data to BT transceiver 106. When forwarding the vital sign data from patient support apparatus to a server on network 80, controller 140 may utilize network transceiver 96 and one or more access points 82.

As noted above, patient support apparatus 20 is also configured to use UWB transceivers 132 to determine the relative position of one or more infusion pumps 100 (FIGS. 4 & 5). Infusion pump 100 includes a UWB transceiver 160, an infusion controller 162, a network transceiver 164, and an infusion pump ID 166 that uniquely identifies each infusion pump 100. UWB transceiver 160 is adapted to communicate with the UWB transceivers 132 positioned onboard patient support apparatus 20 so that the position of infusion pump 100 relative to patient support apparatus 20 can be repetitively determined. UWB transceiver 160 may be the same as all of the other UWB transceivers discussed herein (e.g. UWB transceivers 132, 104, 146, etc.). UWB transceiver 160 is further adapted to transmit the unique ID 166 to patient support apparatus 20 so that patient support apparatus 20 knows which specific infusion pump 100 it is communicating with. As will be discussed in greater detail below, controller 140 may forward this infusion pump ID 166 to patient support apparatus server 84 and server 84 may use the ID 166 for one or more purposes, such as, but not limited to, communicating with EMR server 92, communicating with one or more electronic devices 98, and/or for other purposes.

Controller 162 of infusion pump 100 is adapted to oversee the operation of infusion pump 100, to control what infusion pump data is sent to EMR server 92 via network transceiver 164, and, in some embodiments, to also process the communications of UWB transceiver 160 with other UWB transceivers (e.g. transceivers 132 onboard patient support apparatus 20). Controller 162 may further be adapted, in some embodiments, to forward data regarding its operation to EMR server 92 via network transceiver 164 and access point 82. Such data may then become available to various servers on network 80, such as patient support apparatus server 84, via an HL-7 feed. Such data may include a number, or other identifier, identifying the specific medication being infused, a dosage amount, the flow rate, a concentration of medication, pump ID 166, and/or any other data regarding the identity of, the operation of, and/or the medication being delivered by infusion pump 100.

In some embodiments of infusion pump 100, controller 162 does not communicate with UWB transceiver 160. In such embodiments, UWB transceiver 160 may be part of a UWB tag that is physically attached to infusion pump 100, but that does not communicate with the electronics of infusion pump 100. In such embodiments, the UWB transceiver 160 communicates with transceivers 132 of patient support apparatus 20 independently of the operation of infusion controller 162 and the UWB transceiver 160 does not forward any infusion pump data directly to patient support apparatus 20, other than a unique identifier that uniquely identifies that particular infusion pump 100.

Alternatively, in those embodiments of infusion pump 100 where controller 162 communicates with UWB transceiver 160, controller 162 may oversee the operation of transceiver 160 and use UWB transceiver 160 for communicating directly with one or more of UWB transceiver 132 onboard patient support apparatus 20. Depending upon the particular embodiment of infusion pump 100, this communication between UWB transceiver 160 and one or more UWB transceiver 132 may include any one or more of the following: the transmission of the patient's weight, as measured by scale system 138, from patient support apparatus 20 to infusion pump 100, the transmission of infusion pump data 100 to patient support apparatus 20, the transmission of infusion pump ID 166 that uniquely identifies a particular infusion pump 100 to patient support apparatus 20, the transmission of patient support apparatus identifier 130 from patient support apparatus 20 to infusion pump 100, and/or the transmission of other data between infusion pump 100 and patient support apparatus 20.

In those embodiments of infusion pump 100 where infusion pump 100 transmits infusion data directly to patient support apparatus 20 via UWB transceiver 160 (or via another transceiver incorporated into the infusion pump 100, such as, but not limited to, a Bluetooth transceiver), patient support apparatus 20 may be configured to utilize that infusion pump data to double check to see that medication being delivered to the patient via the infusion pump 100 is not at an incorrectly high dosage, given the patient's weight (as determined by scale system 138). This double checking may be performed directly by circuitry onboard patient support apparatus 20 (e.g. controller 140), or controller 140 may be configured to forward the infusion pump data and patient weight data to server 84 so that server 84 can perform this double-checking function. In either case, if a high dosage level is detected (i.e. one that exceeds a threshold level for a given patient weight), patient support apparatus 20 and/or server 84 are configured to issue an alert to one or more caregivers.

Patient support apparatus 20 may be configured to issue an alert in a number of different manners, including, but not limited to, aural and/or visual alerts. The visual alerts may include the flashing of one or more lights, the display of one or more messages on display 52, and/or the transmission of a signal to the nurse call system 70 via outlet 64. Server 84 may be configured to issue an alert by forwarding a message to one or more electronic devices 98 that are associated with one or more caregivers assigned to the patient onboard patient support apparatus 20. Still other methods of alerting an appropriate caregiver may be implemented.

In order for patient support apparatus 20 and/or server 84 to determine whether a medication is being delivered at too high of a dosage, or at too high of a rate, patient support apparatus 20 and/or server 84 are either provided with, or configured to communicate with, a database containing medications and acceptable dosage levels for the medications given a patient's weight. This database may be stored in server 84, onboard patient support apparatus 20 (e.g. in memory 130), or in another location that server 84 and/or that patient support apparatus 20 can automatically access. The database may be a conventional database, or other type of database. In some embodiments, acceptable dosage and/or rate levels for particular medications may be defined and input by authorized personnel of the healthcare facility, either by accessing server 84 and/or an appropriate control screen on a control panel 54 onboard patient support apparatus 20. Such configurations allow authorized personnel to supplement and/or override information provided in the medication database.

Controller 162 of infusion pump 100 (FIG. 5) may comprise a microcontroller and/or any of the other structures that were mentioned above with respect to controllers 112, 140, and/or 148. Controller 162 is adapted to control the infusion of medication into an IV fluid that is being delivered to a patient. Controller 162 may also be adapted to report data, such as the flow rate, dosage amount, and/or other information to EMR server 92 using network transceiver 164 and/or to patient support apparatus 20 using UWB transceiver 160 (or another transceiver that communicates directly with patient support apparatus 20).

Controller 140 of patient support apparatus 20 is adapted to associate patient support apparatus 20 (or the patient assigned thereto) with a specific medical device (e.g. infusion pump 100, vital sign sensor 150, and/or other types of medical devices) if the medical device is positioned within volume of space 152 (which may vary for different medical devices and/or for other reasons). Controller 140 uses UWB transceivers 132 to determine the relative position of the medical device by communicating with one or more respective UWB transceivers (e.g. transceivers 160 of infusion pumps 100) that are either built into the medical device or attached to a tag that is affixed to the medical device. This determination of the position of the medical device relative to patient support apparatus 20 is used by controller 140 to determine if it will associate the medical device with patient support apparatus 20 and/or the patient assigned thereto. Once associated, controller 140 may be configured to communicate with the medical device in various manners. For example, with respect to infusion pumps 100, controller 140 may be configured to perform any one or more of the following types of communications with an associated infusion pump 100: to send a patient weight to the associated infusion pump 100, to receive infusion pump data from the associated infusion pump 100 and display and/or send it to server 84, to double check the operation of the associated infusion pump 100, and/or to interrogate EMR server 92 for data that came from the associated infusion pump 100, and/or other types of communications.

In some embodiments, controller 140 may be configured to display data from the associated medical device, and/or process the data from the associated medical device, in any of the manners disclosed in commonly assigned U.S. patent application Ser. No. 63/306,279 filed Feb. 3, 2022, by inventors Madhu Sandeep Thota et al. and entitled COMMUNICATION SYSTEM FOR PATIENT SUPPORT APPARATUSES, the complete disclosure of which is incorporated herein by reference.

In some embodiments, patient support apparatus 20 is configurable by a user (e.g. via control panel 54*a*) to control what information, if any, patient support apparatus 20 will send to an associated display device 56, to patient support apparatus server 84, and/or to EMR server 92. Thus, a user can instruct patient support apparatus 20, for example, to send blood pressure readings, breathing rate readings, and pulse rate readings to EMR server 92, but not infusion pump data from infusion pump 100. As another example, patient support apparatus 20 is configurable by a user such that controller 140 will send infusion pump data to display device 56 and patient support apparatus server 84, but not send any vital sign data to any display devices 56, even if controller 140 determines those display devices 56 (or their associated locator unit 60) are within the space volume 152 and associated them with patient support apparatus 20.

Locator units 60 are configured to send a message to patient support apparatuses 20 indicating whether or nota display device 56 is coupled thereto via video port 120. In such embodiments, when controller 140 of patient support apparatus 20 receives the signal indicating that a display device 56 is coupled to an associated locator unit, it is configured to consult the customized user settings to determine whether to send infusion pump data, vital sign data, or other data to that locator unit 60 for forwarding to the display device 56 coupled to video port 120. It bears noting that, when patient support apparatus 20 associates itself with a particular locator unit 60 that has a display device 56 coupled to its video port 120, it is not necessary for the display device 56 to be positioned within space volume 152 in order for controller 140 to send data to be displayed on the display device 56. Instead, controller 140 is configured to only check whether the associated locator unit 60 is positioned within space volume 152. If it is, controller 140 may send (depending upon the user settings) infusion pump data and/or other data to the locator unit 60 for forwarding to the display. If locator unit 60 is not positioned within space volume 152, then controller 140 does not send any data to the locator unit 60 for displaying on display device 56, even if the display device 56 happens to be positioned within space volume 152.

In addition to allowing a user to customize what data, if any, that is sent to a display device 56, controller 140 is further configured to allow a user to customize what data is sent to different types of display devices 56. Thus, controller 140 may be programmed to allow a user to send a first set of data to a display device 56 that is coupled to an associated locator unit 60 and a second set of data, different from the first set of data, to a different display, such as, for example, display 52 of patient support apparatus 20 and/or another display, such as, but not limited to, ones that are incorporated into conventional smart phones, laptop computers, tablet computers, smart TVs and/or smart monitors that are either in communication with patient support apparatus server 84 and/or that are positioned within space volume 152, as determined by one or more UWB transceivers coupled to them that adapted to communicate with UWB transceiver 132 of patient support apparatus 20. It will be appreciated, that in such cases, the conventional smart phone, laptop computer, tablet computer, or other type of display device will include a software app that oversees the UWB communications with patient support apparatus 20 and that controls the display of the data on the display (i.e. screen) of the display device. The software app will have one or more security features built into it that only allow authorized users to have this data displayed on the display device, thereby preventing unauthorized users from viewing this data on their own smart phone, laptop computer, tablet computer, etc. In some embodiments, controller 140 is configured to execute a security check protocol with the display device to authenticate the display device prior to sending it any data for displaying thereon.

Display device 56 (FIG. 5) includes a display controller 170 and a display 172. Controller 140 of patient support apparatus 20 is configured to use UWB transceivers 132 to determine the location of the locator unit 60 to which the display device 56 is coupled. If the locator unit 60 is not positioned within the space volume 152, the controller 140 will not send data to be displayed to the locator unit 60. If the locator unit 60 is positioned within the space volume, the controller 140 is configured to be able to send data to be displayed on the coupled display device 56 by forwarding the data to be displayed to the associated locator unit 60, which then forwards it to display device 56 via video port 120 and video cable 110. In some embodiments, controller 140 forwards the data to be displayed on display device 56 to the associated locator unit 60 by using Bluetooth transceiver 128, while in other embodiments it may use a UWB transceiver 132, or another type of transceiver. The forwarding of data to be displayed on display device 56 is a direct forwarding of data from patient support apparatus 20 to locator unit 60, and from there to display device, with no other intermediaries, in at least some embodiments.

Because display device 56 need not include a UWB transceiver, display device 56 may be a conventional television, computer monitor, or other conventional device, that is capable of displaying the video signals that are transmitted over video cable 110. In addition, it is not necessary for display device 56 to execute any specialized software app that authenticates communication with the coupled locator unit and/or with patient support apparatus 20. Instead, once controller 140 determines that locator unit 60 is within space volume 152 (and, in some cases, determines that locator unit 60 is an authentic locator unit), controller 140 need not perform any additional security protocols regarding display device 56. Indeed, controller 140 does not need to be able to perform any communications with display device 56 other that forwarding data to be displayed to the associated locator unit 60. In this manner, display device 56 need not know anything about locator unit 60 and/or patient support apparatus 20. It merely displays the video signal coming from video cable 110, and therefore does not need a software app that is specialized to patient support apparatus 20 and/or to locator unit 60 and/or to UWB communications.

If controller 140 of patient support apparatus 20 determines that a medical device, such as, but not limited to, an infusion pump 100 is positioned within space volume 152 (using UWB transceivers 132 and 160), it associates that medical device to patient support apparatus 20 and/or the particular patient who is assigned to patient support apparatus 20. This association may be carried out in different manners, and in some embodiments, is carried out, either alone by, or in conjunction with, patient support apparatus server 84. Server 84 may carry out this association by storing in its memory data correlating specific medical device identifiers (e.g. infusion pump identifiers 166, vital sign identifiers 154, etc.)—which are transmitted to patient support apparatus 20 by the medical device, and then forwarded by patient support apparatus 20 to server 84 via network transceiver 96—with specific patient support apparatus identifiers 130. In order to associate specific medical devices with a specific patient, patient support apparatus server 84 uses the location identifier 122 that it receives from a specific patient support apparatus 20 to determine the room location of the specific patient support apparatus 20. From this room location, server 84 receives data from a conventional Admission, Discharge, Tracking, or other server that is coupled to network 80 that identifies a specific patient for a specific room (or bay within a room). Server 84 is then able to correlate a specific medical device with a specific patient identifier because it knows the room (or bay) of the patient support apparatus 20, the specific IDs of the medical devices associated with that particular patient support apparatus 20, and patient identifier associated with that particular room (or bay). After associating a medical device with a particular patient, server 84 is able to automatically retrieve data from a specific patient's medical records stored within EMR server 92 and/or to automatically send data from a particular medical device to the specific patient's medical records stored with EMR server 92.

Patient support apparatus server 84 is also able to determine which HL-7 feeds it will subscribe to based on the patient identifier it associates with a particular patient support apparatus 20 or medical device. For example, if server 84 determines that an infusion pump 100 having an identifier XYZ is located in room 402, and room 402 is currently assigned to Ms. Smith, then server 84 sends a request to EMR server 92 to subscribe to Ms. Smith's infusion pump HL-7 feed. Once server 84 receives data from this HL-7 feed, it forwards relevant portions of the data to the specific patient support apparatus 20 associated with Ms. Smith's infusion pump 100.

Continuing with this example, in some embodiments, server 84 receives the weight of Ms. Smith from the scale system 138 built into her assigned patient support apparatus 20 (which controller 140 sends to server 84 via transceiver 96). Server 84 then uses this weight data and the data from her infusion pump 100 (which it receives from EMR server 92) to double check to see that the rate, amount, and/or dosage she is receiving (as indicated in the infusion pump data from EMR server 92) is appropriate for a person of her weight. This determination may involve using a database containing acceptable dosages by patient weight for different medications, as previously discussed. Further, if server 84 detects that an incorrect dosage may be present, server 84 send out alert information to the patient support apparatus 20 assigned to Ms. Smith, to the electronic device 98 of the caregiver(s) associated with Ms. Smith, and/or to other recipients.

In those embodiments of infusion pump 100 where infusion pump controller 162 is configured to communicate with UWB transceiver 160, controller 140 is configured to transmit the patient's weight to controller 162 via UWB transceiver 160, as was noted. Controller 140 is also able to receive infusion pump data from controller 162 directly via UWB communication between infusion pump 100 and patient support apparatus 20. Controller 140 may then display all or some of this infusion pump data on display 52 and/or an associated display device 56 (and/or may forward some of it to server 84 and/or EMR server 92, and/or perform other actions with this data)

In those embodiments of infusion pump 100 where infusion pump controller 162 is not configured to communicate with UWB transceiver 160 (such as when transceiver 160 is incorporated into a stand-alone tag that is affixed to infusion pump 100, but not in electronic communication with controller 162), server 84 and patient support apparatus 20 may be configured to display data from the infusion pump 100 using an alternate communication path. Specifically, as noted above, server 84 is adapted to retrieve infusion pump data from EMR server 92. Server 84 is configured, in some embodiments, to forward all or some of this infusion pump data to the patient support apparatus 20 associated with that particular patient support apparatus 20 (through network 80, access points 82, and network transceiver 96), and that particular patient support apparatus 20 is then configured to display all or some of that infusion pump data on its display 52 and/or one or more associated display devices 56. In this manner, even though infusion pump controller 162 may not be configured to communicate directly with patient support apparatus 20, patient support apparatus 20 is configured to automatically display all or some of the data from infusion pump 100 on display 52 and/or display device(s) 56. It should be noted that this display of infusion pump data takes place automatically in response to the infusion pump 100 moving inside of space volume 152 and becoming associated with patient support apparatus 20.

Each space volume 152 (FIG. 4) is defined with respect to patient support apparatus 20 and therefore moves as patient support apparatus 20 moves. In some embodiments of locator units 60, each locator unit 60 is programmed with the definition of a separate space volume (not shown) that is fixed with respect to the particular locator unit 60. In such embodiments, controller 140 is configured to use space volume 152 for determining whether a medical device (e.g.

infusion pump 100, vital sign sensor 150, etc.) and/or a display device 56 should be associated with patient support apparatus 20, and to use the space volume defined with respect to a locator unit 60 for determining whether patient support apparatus 20 should be associated with that particular locator unit 60. That is, patient support apparatus 20 is configured to use two different criteria for determining whether to associate a device with patient support apparatus 20—one for locator units 60 and another one for other types of devices, such as display devices 56 and/or medical devices that are used to treat a patient.

In those embodiments of locator unit 60 that store the definition of a space volume defined with respect to the locator unit (i.e. not space volume 152) within their onboard memory, the locator unit 60 may be configured to forward this definition to patient support apparatus 20 for controller 140 to use to determine whether patient support apparatus 20 is positioned within that space volume or not. Alternatively, controller 112 of the locator unit 60 may use this definition of the space volume to determine whether patient support apparatus 20 is positioned inside of the space volume or not, and to then forward the result of this determination to patient support apparatus 20. In either scenario, controller 140 is configured to automatically associate itself to the locator unit 60 if it is positioned inside of the space volume defined with respect to a locator unit 60, or to not associate itself with the locator unit 60 if it is not currently positioned inside of the space volume defined with respect to that locator unit 60.

In those embodiments of patient support apparatus 20 that utilize a locator unit space volume to determine their association to a locator unit 60, controller 140 is configured to not use space volume 152 for determining this association. That is, controller 140 only uses a single space definition for determining the association, or lack of association, between a patient support apparatus 20 and a locator unit 60. Thus, in such embodiments, controller 140 only uses space volume 152 for determining the association of patient support apparatus 20 with one or more medical devices and/or one or more display devices 56.

Although FIG. 5 illustrates a single vital sign sensors 150 and a single infusion pump 100, it will be understood that this is merely for illustration purposes. Multiple vital sign sensors 150, multiple infusion pumps 100, multiple other types of medical devices, and/or any combinations of these devices, may be in use on a particular patient and controller 140 of patient support apparatus 20 is adapted to determine the locations of those devices relative to space volume 152, and, if they are positioned inside of space volume 152, to automatically associate them with patient support apparatus 20 and make their data available for display, forward their data to patient support apparatus server 84, and/or take other actions.

In some embodiments, controller 140 is adapted to automatically associate itself with any one or more of the medical devices disclosed in commonly assigned U.S. patent application 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosure of which is incorporated herein by reference. Patient support apparatus 20 is configurable by a user to also, or alternatively, automatically display any of the data from these other types of medical devices on any of the displays 52 and/or associated display devices 56 when these medical devices are associated with patient support apparatus 20.

It should also be noted that the display of data from the associated medical devices on display 52 and/or display devices 56 is carried out by patient support apparatus 20 automatically. That is, for example, when a user has configured patient support apparatus 20 to display a patient's heart rate and/or infusion pump data on a display device 56, it automatically forwards the heart rate data and/or infusion pump data to the associated display device 56. Consequently, if a patient with a heart rate monitor 150 and an infusion pump 100 is wheeled into a bay area of a patient room that includes a display device 56 coupled to a locator unit 60, controller 140 is configured to automatically start displaying the patient's heart rate information and infusion pump data on that display device 56 as soon as patient support apparatus 20 completes the following three association processes: (1) the association between patient support apparatus 20 and the locator unit 60 to which display device 56 is coupled, (2) the association between patient support apparatus 20 and the heart rate monitor 150, and (3) the association between patient support apparatus 20 and the infusion pump 100. In this manner, the caregiver sees the patient's heart rate and infusion pump data displayed on the display device 56 within seconds after moving the patient support apparatus 20 into the bay area, and the caregiver doesn't need to connect any cables, press any buttons, or take any other actions, in order for the heart rate data and/or infusion pump data to be displayed on display device 56. Similarly, when the patient support apparatus 20 moves out of the bay area, the display of the patient's data on the display device 56 automatically terminates. This automatic termination is carried out after patient support apparatus 20 moves outside of the space volume associated with the locator unit 60 to which the display device 56 is connected. Once outside of this space volume, controller 140 disassociates patient support apparatus 20 with that locator unit 60 and its associated display device 56, and once this disassociation occurs, it stops sending data to be displayed on display device 56.

As another example of the automatic display of medical device data on a display, if a caregiver approaches a patient support apparatus 20 while carrying a portable electronic device 98—such as a smart phone or tablet computer that includes a display, a UWB transceiver, and the appropriate software app—controller 140 is adapted to automatically start forwarding the patient's data to the portable electronic device 98 for display on its screen. In this manner, a caregiver that brings his or her portable electronic device within space volume 152 can have that patient's heart rate data (and/or other data) automatically displayed on his/her device. When the caregiver moves his or her portable electronic device 98 outside of the space volume 152, the display of that patient's data automatically ceases because controller 140 automatically disassociates patient support apparatus 20 from the portable electronic device 98 and stops sending it data to be displayed. If the caregiver then moves to another patient's patient support apparatus 20 and steps inside the space volume 152 of that patient support apparatus, he or she will automatically see the data from the medical devices associated with that patient displayed on his or her portable electronic device 98.

The automatic display of data on one or more display devices 56, and/or the automatic double-checking of infusion pump data, is able to be carried out by controller 140 and/or server 84 because controller 140 repetitively determines the relative location of patient support apparatus 20 to infusion pump 100 (and other medical devices) and to locator units 60. In addition, when controller 140 detects that one or more of these devices are within communication range, it automatically determines whether they are positioned within space volume 152 (or, for locator units 60, the space volume associated with that locator unit 60) and, if they are, it automatically associates them to patient support apparatus 20. Once this association is made, the process of forwarding information for display on display device 56 is carried out automatically. Similarly, once this association is made, the process of double-checking infusion pump data based on patient weight is also carried out automatically.

It will be understood that the frequency at which controller 140 repetitively determines the relative location of infusion pumps 100, other medical devices, and locator units 60, may vary in different embodiments. In some embodiments, this occurs multiple times a second. In other embodiments, this occurs less frequently than once a second. In still other embodiments, the frequency at which controller 140 determines the relative position of a device to patient support apparatus 20 may vary according to the device, the current location of patient support apparatus 20, the movement state of patient support apparatus 20 (i.e. whether it is currently moving or stationary), the brake state of patient support apparatus (i.e. whether the brake is on or off), and/or according to one or more other factors.

In those embodiments of patient support apparatus 20 where controller 140 is configured to associate itself with locator units 60 based on a space volume defined with respect to a locator unit 60, rather than space volume 152, locator units 60 may be configured to send the dimensions of their space volume to the patient support apparatus 20 for controller 140 to use when determining whether to associate with that locator unit 60 or not. Alternatively, or additionally, patient support apparatus 20 may store in its memory 134 the dimensions of the space volumes assigned to each locator unit 60. As yet another alternative, controller 140 may not need to know the dimensions of the space volumes assigned to locator units 60 at all, but instead may await a message sent by locator unit 60 to patient support apparatus 20 indicating whether the patient support apparatus 20 should be associated with the locator unit 60 based on locator unit 60's own determination of whether the patient support apparatus 20 is currently positioned within the space volume it has defined and stored in its own internal memory.

It will be understood that in any of the embodiments of patient support apparatus 20 discussed herein, the size, shape, location, and/or other aspects of space volume 152 may be changed by controller 140 when determining whether to disassociate a device, rather than to associate a device. In other words, once a device has been determined to be positioned inside of a space volume 152, controller 140 may increase the size of—and/or otherwise change one or more dimensions of—the space volume 152, when determining whether to disassociate the device. In this manner, space volume 152 may have a sort of hysteresis aspect wherein a device has to be positioned inside of a smaller space volume 152 in order to be associated with another device, but thereafter can only be disassociated if it moves outside of a larger sized space volume 152. In still other embodiments, the dimensions of space volumes 152 are the same for both association and disassociation purposes.

Patient support apparatus 20 may include one or more screens that are displayable on display 52 that allow a user to customize the data from associated medical devices that is shown on display 52 and/or display devices 56. In addition, patient support apparatus 20 is configured to allow the user to change the format and/or layout in which the selected data is to be displayed.

The term "associates," or its variants, as used herein, refers to the identification by controller 140 (or server 84) of which devices (locator units 60, infusion pumps 100, vital sign sensors 150, and/or other devices) are intended for use with the patient assigned to patient support apparatus 20 and/or that are intended for use by patient support apparatus 20 at a particular location within a healthcare facility. For locator units 60, patient support apparatus 20 associates itself with only a single locator unit 60 at a given time. For linked locator units 60, the associated linked locator unit 60 is the linked locator unit 60 that controller 140 will send data to for forwarding to the adjacent communication outlet 64, as well as the linked locator unit 60 that controller 140 will receive data from that originated from communication outlet 64. The associated locator unit 60 is therefore the locator unit 60 that patient support apparatus 20 will send the patient's voice signals to (and/or exit detection alerts to) for forwarding to nurse call system 70. It is also the locator unit 60 that controller 140 will send television commands to when a patient onboard patient support apparatus 20 activates one or more of the television controls **50*l*-50*r*. Similarly, it is the locator unit that controller 140 will send light commands to when a patient onboard patient support apparatus 20 activates one or more or the reading or room light controls 50*s* or 50*t*. The linked locator unit 60 that patient support apparatus 20 associates itself with is also the locator unit 60 that patient support apparatus will receive audio signals from and direct to its onboard speaker(s). Such audio signals may correspond to voice signals from a remotely positioned nurse that are forwarded to the corresponding communication outlet 64 by way of nurse call system 70, or such audio signals may correspond to television audio signals that are routed from television 72 to communication outlet 64 by way of the one or more conductors 68**.

Generally speaking, controller 140 is configured to associate with an unlinked locator unit if patient support apparatus 20 moves inside of that unlinked locator unit's space volume. In an alternative embodiment, controller 140 may be configured to associate with an unlinked locator unit 60 if the patient support apparatus 20 moves close enough to the unlinked locator unit 60 such that the locator unit 60 is positioned inside of space volume 152. In still other embodiments, the unlinked locator units 60 that controller 140 associates with may be the nearest unlinked locator unit 60 that is in the same room as, or on the same side of a wall as, patient support apparatus 20.

For medical devices, such as infusion pumps 100 and vital sign sensors 150, the medical devices that controller 140 associates with patient support apparatus 20 are those devices that are used on the patient who is currently assigned to patient support apparatus 20. As noted, controller 140 associates these devices to a particular patient support apparatus 20 when it determines that these devices are currently positioned inside of space volume 152. In some embodiments, controller 140 presumes that whichever patient is currently occupying patient support apparatus 20 is the patient assigned to patient support apparatus 20.

The task of associating and disassociating a particular patient to a particular patient support apparatus 20 may be carried out locally by controller 140, or it may be carried out remotely by patient support apparatus server 84. Such remote association generally involves patient support apparatus server 84 using information from a conventional Admissions, Discharge, and Transfer (ADT) server or EMR server 92 on network 80 to determine the room location (e.g. room number and/or bed bay ID) of a particular patient, and then matching that room location with the room location of a particular patient support apparatus 20 (which is reported to server 84 by the patient support apparatuses 20 which use locator units 60 to determine their location). In other words, server 84 consults a conventional server on network 80 that correlates specific patients to specific room numbers and/or bay areas, such as an ADT and/or EMR server 92, and then uses the known room numbers and/or bay areas of specific patient support apparatuses 20 to match a specific patient to a specific patient support apparatus 20.

Alternatively, or additionally, manual association of a particular patient support apparatus 20 to a particular patient and/or to a particular device may be carried out in a variety of different manners. One manner involves incorporating a bar code scanner and/or near field sensor into patient support apparatus 20 that is adapted to read the bar code and/or near field patient ID data contained within a conventional patient wristband and/or a medical device (or a tag attached to the medical device). When a patient is assigned to a particular patient support apparatus 20, the caregiver scans the patient's wristband using the bar code or near field scanner that is built into the patient support apparatus 20. The patient ID data that is read from the wristband is then forwarded to server 84, which may distribute it to an EMR server and/or to other servers on the network 80. Similarly, when a device is used with a particular patient, the caregiver scans the bar code or near field transceiver coupled to the device and receives an ID from the device. Controller 140 then associates the device having that particular device ID with patient support apparatus 20.

In some embodiments of patient support apparatus 20, controller 140 forwards information to patient support apparatus server 84 so that server 84 can determine whether to associate a particular device with a particular patient support apparatus 20. In such embodiments, server 84 sends a message back to patient support apparatus 20 informing it of what devices should be associated with, and what devices should not be associated with, patient support apparatus 20.

In some embodiments, when patient support apparatus 20 and/or server 84 associate a device with a particular patient support apparatus 20, controller 140 and/or server 84 are configured to inform medical personnel (via electronic devices 98) that the device is associated with a particular patient support apparatus 20 and/or with a particular patient assigned to that patient support apparatus 20. In this manner, data from the device can be correlated with a particular patient, room location, and/or patient support apparatus 20. Patient support apparatus 20 may therefore be configured to automatically forward data from the associated medical devices to server 84 after the devices become associated with patient support apparatus 20. Such data may, in turn, be automatically forwarded by server 84 to an EMR server for entry into the corresponding patient's electronic medical record. In this manner, once controller 140 associates a device with the patient support apparatus 20, data from the device can be automatically recorded in that patient's particular electronic medical record without requiring the caregiver to either manually associate the device with the patient and/or with the patient support apparatus 20 assigned to that patient. In other words, because controller 140 automatically determines that the device is positioned within space volume 152, it is not necessary for a caregiver to take any manual steps to ensure that data from the device is forwarded to the proper corresponding patient's electronic medical record because patient support apparatus 20, along with server 84, automatically determine the correct patient associated with that medical device. Further details regarding at least one manner in which this automatic patient determination may be made are found in commonly assigned U.S. patent application Ser. No. 63/193,777 filed May 27, 2021, by inventors Thomas Deeds et al. and entitled SYSTEM FOR ASSOCIATING MEDICAL DEVICE DATA, the complete disclosure of which is incorporated herein by reference.

In addition, the aforementioned '777 patent discloses several manners in which a UWB tag may be constructed. Such tags may be attached to infusion pumps 100, vital sign sensors 150 and/or to other medical devices used with patient support apparatus 20. The use of such tags allows controller 140 to automatically determine the position of infusion pumps 100, vital sign sensors 150 and/or other medical devices that don't have their own built-in UWB transceivers, but that instead have a UWB tag attached to them.

In general, the tag attached to a device includes a UWB transceiver that is able to communicate with each UWB transceiver 132 onboard patient support apparatus 20. This communication enables controller 140 of patient support apparatus 20 to determine the distances between each UWB transceiver 132 and the tag. By knowing these distances, as well as the location of each transceiver 132 on patient support apparatus 20, controller 140 is able to determine the relative position of the tag with respect to patient support apparatus 20, including whether the tag is positioned inside or outside of space volume 152.

It will be understood controller 140 is configured to automatically associate and disassociate patient support apparatus 20 with a variety of different devices using UWB transceiver 132. These devices include, but are not limited to, exercise devices, heel care boots, IV stands and/or poles, ventilators, patient monitors (e.g. saturated oxygen ($Sp0_2$) monitors), patient positioning devices (e.g. wedges, turning devices, pumps), ambient sensors (e.g. air temperature, air flow, light, humidity, pressure, altitude, sound/noise), and/or any other types of devices that are used in the treatment, monitoring, and/or rehabilitation of the patient. Such devices merely need to include a UWB transceiver built therein, or attached thereto, that is able to communicate with UWB transceiver 132 positioned onboard patient support apparatus 20.

In some embodiments, UWB transceivers 104, 132, 146, and 160 may operate in the same manner as, and include any of the same functions as, the anchors and pseudo-anchors disclosed in commonly assigned U.S. patent application Ser. No. 63/193,777 filed May 27, 2021, by inventors Thomas Deeds et al. and entitled SYSTEM FOR ASSOCIATING MEDICAL DEVICE DATA, the complete disclosure of which has already been incorporated herein by reference.

In some embodiments, locator units 60 may also be configured to determine the location of a device (e.g. infusion pump 100, vital sign sensor 150, etc.) in any of the manners disclosed in commonly assigned U.S. patent application Ser. No. 63/132,514 filed Dec. 31, 2020, by inventors Alexander Bodurka et al. and entitled PATIENT SUPPORT APPARATUS AND MEDICAL DEVICE NETWORKS, and in commonly assigned U.S. patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosures of both of which are incorporated herein by reference.

In any of the embodiments disclosed herein, server 84 may be configured to additionally execute a caregiver assistance software application of the type described in the following commonly assigned patent applications: U.S. patent application Ser. No. 62/826,97, filed Mar. 29, 2019 by inventors Thomas Durlach et al. and entitled PATIENT CARE SYSTEM; U.S. patent application Ser. No. 16/832,760 filed Mar. 27, 2020, by inventors Thomas Durlach et al. and entitled PATIENT CARE SYSTEM; and/or PCT patent application serial number PCT/US2020/039587 filed Jun. 25, 2020, by inventors Thomas Durlach et al. and entitled CAREGIVER ASSISTANCE SYSTEM, the complete disclosures of which are all incorporated herein by reference. That is, server 84 may be configured to share with one or more electronic devices 98 any of the information shared with the electronic devices disclosed in these aforementioned patent applications. Thus, for example, server 84 may be configured to not only share the location of patient support apparatuses 20 (and any medical devices that may be associated with them) with electronic devices 98, but it may also forward to devices 98 patient vital sign data, infusion pump data, patient support apparatus status data (e.g. current siderail position, bed exit status, brake status, height status, scale data, etc.) and/or caregiver rounding data (e.g. when the last rounding was performed for a particular patient, when the next rounds are due, etc.).

It will also be understood that the number of UWB transceivers on patient support apparatus 20 may vary. In some embodiments, patient support apparatus 20 includes three UWB transceivers 132 positioned at known locations on patient support apparatus 20 that are stored in memory 134. In other embodiments, four UWB transceivers 132 are included. In still other embodiments, fewer than three UWB transceivers 132 are used, such as only a single UWB transceiver or two transceivers. Still other numbers of UWB transceivers 132 may be included.

In some embodiments, locator units 60 may include additional information stored therein that is shared with patient support apparatus 20 when patient support apparatus 20 becomes associated with the locator unit 60. Such additional information may include location information identifying the relative position of the locator unit 60 with respect to one or more other locator units 60 that are positioned nearby. Additionally or alternatively, the locator units 60 may include information regarding the thickness and/or materials of the wall 62 to which it is attached, wherein such information provides an indication to the patient support apparatus 20 of the amount of attenuation that UWB signals will likely experience when traveling through that wall. Additionally or alternatively, the locator units 60 may include information identifying their general location within the healthcare facility (e.g. room 400, bay A of room 302, hallway X, maintenance area Y, radiology department, emergency department, etc.) and/or information identifying a more specific location of the locator units 60 within the healthcare facility (e.g. a set of X,Y,Z coordinates in a frame of reference that includes all, or a portion of, the healthcare facility; a height on the wall 62, a distance from one or more landmarks and/or architectural features within the healthcare facility, and/or other more specific information). In some embodiments, patient support apparatus 20 is adapted to utilize this information to determine its location within the healthcare facility and/or to determine whether it is positioned on the same side of the wall 62 as a particular locator unit 60. In some embodiments, patient support apparatus 20 and/or locator units 60 include any of the same structures, functions, and/or features of any of the patient support apparatuses and/or wall units disclosed in commonly assigned U.S. patent application Ser. No. 63/245,245 filed Sep. 17, 2021, by inventors Kirby Neihouser et al. and entitled SYSTEM FOR LOCATING PATIENT SUPPORT APPARATUSES, the complete disclosure of which has already been incorporated herein by reference.

It will also be understood that, although the foregoing description has discussed the use of an HL-7 feed to retrieve patient data from EMR server 92, other types of information conduits and/or protocols may be used. Thus, for example, patient support apparatus server 84 may retrieve patient data, such as, but not limited to, infusion pump data, from EMR server 92 using whatever type of data exchange functionality is built into that particular EMR server 92, or that is built into a software middleware product that oversees communication with EMR server 92.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a support surface adapted to support a patient;

a scale system adapted to determine a weight of the patient;

a first transceiver coupled to a first location on the patient support apparatus;

a second transceiver coupled to a second location on the patient support apparatus;

a third transceiver coupled to a third location on the patient support apparatus; and a controller adapted to use radio frequency (RF) communication between the first, second, and third transceivers and an infusion pump to determine a position of the infusion pump relative to the patient support apparatus, the controller further adapted to receive an identifier from the infusion pump and to determine if the infusion pump is positioned inside or outside of a volume of space.

2. The patient support apparatus of claim 1 wherein the controller is further adapted to send both the weight of the patient and the infusion pump identifier to a server if the infusion pump is positioned inside the volume of space.

3. The patient support apparatus of claim 2 wherein the first transceiver, the second transceiver, and the third transceiver are all ultra-wideband transceivers, and wherein the patient support apparatus further includes a memory in which the first location, the second location, and the third location of the first, second, and third transceivers, respectively, is stored.

4. The patient support apparatus of claim 3 wherein the controller is further adapted to use the stored locations of the first, second, and third transceivers to determine whether the infusion pump is positioned inside or outside of the volume of space.

5. The patient support apparatus of claim 2 wherein the controller is further adapted to not send the infusion pump identifier to the server if the infusion pump is positioned outside of the volume of space.

6. The patient support apparatus of claim 2 wherein the controller is further adapted to perform the following: use RF communication between the first, second, and third transceivers and a fixed locator to determine a position of the patient support apparatus relative to the fixed locator; receive an identifier from the fixed locator; determine if the patient support apparatus is positioned within a threshold distance to the fixed locator; and forward the fixed locator identifier to the server if the patient support apparatus is positioned within the threshold distance.

7. The patient support apparatus of claim 6 further comprising a microphone positioned onboard the patient support apparatus, the microphone adapted to convert sounds of the patient's voice to audio signals, and wherein the controller is further adapted to transmit the audio signals to the fixed locator if the fixed locator is positioned within the threshold distance, and to not transmit the audio signals to the fixed locator if the fixed locator is positioned outside of the threshold distance.

8. The patient support apparatus of claim 2 wherein the controller is further adapted to receive a message from the server if the infusion pump is determined to be inside the volume of space, wherein the message indicates dosage information regarding a medication being delivered to the patient via the infusion pump, and wherein the controller is further adapted to issue an alert if the dosage information exceeds a threshold, wherein the threshold is based on the weight of the patient.

9. The patient support apparatus of claim 2 further comprising a display in communication with the controller, and wherein the controller is adapted to display data from the infusion pump on the display if the infusion pump is positioned inside the volume of space, and to not display data from the infusion pump on the display if the infusion pump is positioned outside of the volume of space.

10. The patient support apparatus of claim 2 wherein the controller is further adapted to perform the following: receive dosage information from the server relating to the infusion pump if the infusion pump is positioned inside the volume of space, and issue an alert to a caregiver if the dosage information exceeds a threshold, wherein the threshold is based on the weight of the patient.

11. A patient support apparatus comprising:

a support surface adapted to support a patient;

a scale system adapted to determine a weight of the patient;

a first transceiver coupled to a first location on the patient support apparatus;

a second transceiver coupled to a second location on the patient support apparatus;

a third transceiver coupled to a third location on the patient support apparatus; and a controller adapted to use radio frequency (RF) communication between the first, second, and third transceivers and an infusion pump to determine a position of the infusion pump relative to the patient support apparatus, the controller further adapted to determine if the infusion pump is positioned inside or outside of a volume of space, and to send an identifier of the patient support apparatus to the infusion pump if the infusion pump is positioned inside the volume of space.

12. The patient support apparatus of claim 11 wherein the controller is further adapted to send the weight of the patient to the infusion pump if the infusion pump is positioned inside the volume of space.

13. The patient support apparatus of claim 12 wherein the first transceiver, the second transceiver, and the third transceiver are all ultra-wideband transceivers, and wherein the patient support apparatus further includes a memory in which the first location, the second location, and the third location of the first, second, and third transceivers, respectively, is stored.

14. The patient support apparatus of claim 13 wherein the controller is further adapted to use the stored locations of the first, second, and third transceivers to determine whether the infusion pump is positioned inside or outside of the volume of space.

15. The patient support apparatus of claim 14 wherein the controller is further adapted to not send the weight of the patient to the infusion pump if the infusion pump is positioned outside of the volume of space.

16. The patient support apparatus of claim 15 wherein the controller is further adapted to perform the following: use RF communication between the first, second, and third transceivers and a fixed locator to determine a position of the patient support apparatus relative to the fixed locator; receive an identifier from the fixed locator; determine if the patient support apparatus is positioned within a threshold distance to the fixed locator; and forward fixed locator identifier to a server if the patient support apparatus is positioned within the threshold distance.

17. The patient support apparatus of claim 16 further comprising a microphone positioned onboard the patient support apparatus, the microphone adapted to convert sounds of the patient's voice to audio signals, and wherein the controller is further adapted to transmit the audio signals to the fixed locator if the fixed locator is positioned within the threshold distance, and to not transmit the audio signals to the fixed locator if the fixed locator is positioned outside of the threshold distance.

18. The patient support apparatus of claim 16 wherein the controller is further adapted to receive a message from the server if the infusion pump is determined to be inside the volume of space, wherein the message indicates dosage information regarding a medication being delivered to the patient via the infusion pump, and wherein the controller is further adapted to issue an alert if the dosage information exceeds a threshold, wherein the threshold is based on the weight of the patient.

19. The patient support apparatus of claim 13 further comprising a display in communication with the controller, and wherein the controller is adapted to display data from the infusion pump on the display if the infusion pump is positioned inside the volume of space, and to not display data from the infusion pump on the display if the infusion pump is positioned outside of the volume of space.

20. The patient support apparatus of claim 16 wherein the controller is further adapted to perform the following: receive dosage information from the server relating to the infusion pump if the infusion pump is positioned inside the volume of space, and issue an alert to a caregiver if the dosage information exceeds a threshold, wherein the threshold is based on the weight of the patient.

* * * * *